(12) United States Patent
Pe'ery et al.

(10) Patent No.: US 9,849,146 B2
(45) Date of Patent: *Dec. 26, 2017

(54) INHIBITION OF NONSENSE MEDIATED MRNA DECAY BY DRUGS THAT PREVENT HYPUSINATION OF EUKARYOTIC INITIATION FACTOR 5A

(75) Inventors: Tsafi Pe'ery, Montclair, NJ (US); Michael B. Mathews, Montclair, NJ (US); Mainul Hoque, North Arlington, NJ (US); Hartmut M. Hanauske-Abel, Edgewater, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 58 days.

This patent is subject to a terminal disclaimer.

(21) Appl. No.: 14/126,342

(22) PCT Filed: Jun. 13, 2012

(86) PCT No.: PCT/US2012/042272
§ 371 (c)(1),
(2), (4) Date: Mar. 17, 2014

(87) PCT Pub. No.: WO2012/174126
PCT Pub. Date: Dec. 20, 2012

(65) Prior Publication Data
US 2014/0206637 A1 Jul. 24, 2014
US 2017/0319612 A9 Nov. 9, 2017

Related U.S. Application Data

(63) Continuation-in-part of application No. 12/840,270, filed on Jul. 20, 2010, now Pat. No. 8,603,814.

(60) Provisional application No. 61/496,378, filed on Jun. 13, 2011, provisional application No. 61/271,409, filed on Jul. 20, 2009.

(51) Int. Cl.
| A61K 31/4412 | (2006.01) |
| A61K 31/7105 | (2006.01) |
| A61K 31/7064 | (2006.01) |
| A61K 31/4375 | (2006.01) |
| A61K 45/06 | (2006.01) |
| A61K 31/4418 | (2006.01) |
| A61K 31/502 | (2006.01) |
| A61K 31/5025 | (2006.01) |
| A61K 31/7036 | (2006.01) |
| A61K 31/7048 | (2006.01) |

(52) U.S. Cl.
CPC ...... *A61K 31/7105* (2013.01); *A61K 31/4375* (2013.01); *A61K 31/4412* (2013.01); *A61K 31/4418* (2013.01); *A61K 31/502* (2013.01); *A61K 31/5025* (2013.01); *A61K 31/7036* (2013.01); *A61K 31/7048* (2013.01); *A61K 31/7064* (2013.01); *A61K 45/06* (2013.01)

(58) Field of Classification Search
None
See application file for complete search history.

(56) References Cited

U.S. PATENT DOCUMENTS

| 2,540,218 | A | 2/1951 | Shaw |
| 4,797,409 | A | 1/1989 | Lohaus et al. |
| 5,087,616 | A | 2/1992 | Myers et al. |
| 5,789,426 | A | 8/1998 | Hanauske-Abel et al. |
| 5,849,587 | A | 12/1998 | Hanauske-Abel et al. |
| 5,965,585 | A | 10/1999 | Hanauske-Abel et al. |
| 5,965,586 | A | 10/1999 | Hanauske-Abel et al. |
| 6,080,766 | A | 6/2000 | Hanauske-Abel et al. |
| 6,992,096 | B2 * | 1/2006 | Karp ............... A61K 31/4245 514/364 |
| 7,049,328 | B2 | 5/2006 | Spino et al. |
| 8,603,814 | B2 | 12/2013 | Pe'ery et al. |
| 9,271,998 | B2 * | 3/2016 | Pe'ery ............... A61K 31/426 |
| 2006/0275762 | A1 | 12/2006 | Saigo et al. |
| 2007/0031844 | A1 | 2/2007 | Khvorova et al. |

FOREIGN PATENT DOCUMENTS

| WO | 2011/005566 A2 | 1/2011 |
| WO | WO2011/005566 A2 | 1/2011 |

OTHER PUBLICATIONS

Trecartin et al., "Beta-0-Thalassemia in Sardinia is Caused by a Nonsense Mutation" J. Clin. Invest (1981) vol. 68 pp. 1012-1017.*
Ainsworth, "Running the Red Light" Nature (2005) vol. 43818 pp. 726-728.*
Schrader et al., "Temperature-sensitive eIF5A Mutant Accumulates Transcripts Targeted to the Nonsense-mediated Decay Pathway" The Journal of Biological Chemistry (2006) vol. 281 No. 46 pp. 35336-35346.*
Clement et al., "The Antifungal Drug Ciclopirox Inhibits Deoxyhypusine and Proline Hydroxylation, Endothelial Cell Growth and Angiogenesis In Vitro" International Journal of Cancer (2002) vol. 100 pp. 491-498.*
Brunskill, et al., Oral deferiprone for iron chelation in people with thalassaemia (Review), The Cochrane Library, 2009, Issue 1, pp. 1-53, especially p. 2, wherein "adverse events" were recorded in trials comparing deferiprone and DFO.
Olivieri, et al., Long-term Safety and Effectiveness of Iron-Chelation therarpy with Deferiprone for Thalassemia major, The New England Journal of Medicine, 1998, vol. 339(7), pp. 417-423.
Woeller, et al. "NMD resulting from encephalomyocarditis virus IRES-directed translation initiation seems to be restricted to CBP80/20-bound mRNA." EMBO Rep. 9(5): 446-51. (2008).

(Continued)

*Primary Examiner* — Eric S Olson
(74) *Attorney, Agent, or Firm* — Fox Rothschild LLP

(57) ABSTRACT

Provided are methods for treating a NAD comprising administering to a patient suffering from a NAD an inhibitor of NMD and a nonsense suppressor, whereby degradation of NMD susceptible mRNA is decreased and translation termination at a misplaced nonsense codon is blocked.

5 Claims, 9 Drawing Sheets

(56) References Cited

OTHER PUBLICATIONS

Hogue, et al. "Inhibition of HIV-1 gene expression by Ciclopirox and Deferiprone, drugs that prevent hypusination of eukaryotic initiation factor 5A." Retrovirology 6:90. (2009).
Wadhwa, et al. "Receptor Mediated Glycotargeting". Journal of Drug Targeting 3: 111-127. (1995).
Woeller, et al: "NMD resulting from encephalomyocarditis virus IRES-directed translation initiation seems to be restricted to CBP80/ 20-bound mRNA." EMBO Rep. 9(5): 446-51. (2008).
Hoque, et al: "Inhibition of HIV-1 gene expression by Ciclopirox and Deferiprone, drugs that prevent hypusination of eukaryotic initiation factor 5A." Retrovirology 6:90. (2009).
Wadhwa, et al: "Receptor Mediated Glycotargeting". Journal of Drug Targeting 3: 111-127. (1995).
Olivieri, et al: Long-term Safety and Effectiveness of Iron-Chelation Therapy with Deferiprone for Thalassemia Major, The New England Journal of Medicine, 1998, vol. 339(7), pp. 417-423.
Welch EM, et al: "PTC124 Targets Genetic Disorders Caused by Nonsense Mutations", May 3, 2007, Nature, vol. 447, pp. 87-93.
Filosa, et al: "Long-Term Treatment with Deferiprone Enhances Left Centricular Ejection Function When Compared to Deferoxamine in Patients with Thalassemia Major", Blood Cells, Molecules and Diseases, 2013, vol. 51, pp. 85-88.
Borgna-Pignatti et al: "Cardiac Morbidity and Mortality in Deferoxamine- or Deferiprone-Treated Patients with Thalassemia Major", Blood, May 1, 2006, vol. 107, pp. 3733-3737.
Alpendurada et al: "Effects of Combined Deferiprone with Deferoxamine on Right Ventricular Function in Thalassaemia Major", 2012, Journal of Cardiovascular Magnetic Resonance, vol. 14, No. 8, pp. 1-10.
D.J. Weatherall: "Phenotype-Genotype Relationships in Monogenic Disease: Lessons From the Thalassaemias", Apr. 2001, Nature Reviews / Genetics, vol. 2, pp. 245-255.
Voskaridou et al: "Successful Chelation Therapy with the Combination of Deferasirox and Deferiprone in a Patient with Thalassaemia Major and Persisting Severe Iron Overload After Single-Agent Chelation Therapies", 2011, British Journal of Haematology, vol. 154, pp. 654-665.
Wu, et al: "Combined Therapy with Deferiprone and Desferrioxamine Successfully Regresses Severe Heart Failure in Patients with B-Thalessemia Major", 2004, Ann Hematol, vol. 83, pp. 471-473.
Smith, et al: "Effect of Deferiprone or Deferoxamine on Right Ventricular Function in Thalassemia Major Patients with Myocardial Iron Overload", 2011, Journal of Cardiovascular Magnetic Resonance, vol. 13, No. 34, pp. 1-7.
Piga, et al: "Comparative Effects of Deferiprone and Deferoxamine on Survival and Cardiac Disease in Patients with Thalassemia Major: A Retrospective Analysis", May 2003, Haematologica/Journal of Hematology, vol. 88, No. 5, pp. 489-496.
Pepe, et al: "Deferasirox, Deferiprone and Desferrioxamine Treatment in Thalassemia Major Patients: Cardiac Iron and Function Comparison Determined by Quantitative Magnetic Resonance Imaging", 2011, Haematologica, vol. 96, No. 1, pp. 41-47.
Keeling, et al: "Therapies of Nonsense_Associated Diseases", ResearchGate, pp. 1-17 [retrieved on Oct. 28, 2016].
Linde, et al: "Nonsense-Mediated MRNA Decay Affects Nonsense Transcript Levels and Governs Response of Cystic Fibrosis Patients to Gentamicin", Mar. 2007, The Journal of Clinical Investigation, vol. 117, No. 3, pp. 683-692.
Kuzmiak, et al: "Applying Nonsense-Mediated MRNA Decay Research to the Clinic: Progress and Challenges", Jul. 2006, Trends in Molecular Medicine, vol. 12, No. 7, pp. 306-316.
Bhuvanagiri, et al: "NMD: RNA Biology Meets Human Genetic Medicine", Biochem J., 2010, vol. 430, pp. 365-377.
Durand, et al: "Inhibition of Nonsense-Mediated MRNA Decay (NMD) by a New Chemical Molecule Reveals the Dynamic of NMD Factors in P-Bodies", Sep. 24, 2007, The Journal of Cell Biology, vol. 178, No. 7, pp. 1145-1160.
Bidou, et al: "Premature Stop Codons Involved in Muscular Dystophies Show a Broad Spectrum of Readthrough Efficiencies in Response to Gentamicin Treatment", 2004, Gene Therapy, No. 11, pp. 619-627.

\* cited by examiner

INHIBITION OF NONSENSE MEDIATED MRNA DECAY BY DRUGS THAT PREVENT HYPUSINATION OF EUKARYOTIC INITIATION FACTOR 5A

CROSS REFERENCE TO RELATED APPLICATIONS

The instant application is the 35 U.S.C. §371 National Phase Application of International Application Serial No. PCT/US2012/042272, filed Jun. 13, 2012, which claims priority under 35 U.S.C. §119(e) to U.S. Provisional Application No. 60/496,378, filed Jun. 13, 2012, and is also a continuation-in-part of U.S. application Ser. No. 12/840,270, filed Jul. 20, 2010, which claims 35 U.S.C. §119(e) priority to U.S. Provisional Application No. 61/271,409, filed Jul. 20, 2009, all of which are incorporated by reference in their entirety.

FIELD OF THE INVENTION

The present invention relates to methods of treating nonsense-associated diseases and inhibiting nonsense-mediated mRNA decay by administering an inhibitor of NMD and a nonsense suppressor.

BACKGROUND OF THE INVENTION

Nonsense-mediated decay ("NMD") is a cellular mechanism that selectively degrades faulty messenger RNA ("mRNA") containing an out-of-place stop (nonsense) codon. If translated, such mRNAs would produce a shortened version of the encoded protein. The NMD surveillance mechanism reduces or prevents the formation of these defective proteins and peptides. While NMD helps to protect against occasional mistakes that occur during RNA production, it also contributes to a number of genetic disorders collectively termed nonsense-associated diseases ("NADs"). Examples of NADs are cystic fibrosis and Hurler's syndrome. Depending on the gene affected and the mutation, prematurely terminated proteins may have low biological activity, no biological activity, or may even be harmful to biological functions.

In NADs there is usually an insufficient amount of the full-length protein as a result of two processes: (1) the destruction of the defective mRNA by NMD; and (2) the synthesis of truncated protein from mRNA that escapes the destruction. Currently, there are a number of drugs that are partially effective against NADs and function by suppressing nonsense codon recognition (i.e., inhibition of process (2)). NMD is triggered by a premature stop codon located at least 50-55 nucleotides upstream of a splice junction in a multi-exon mRNA. Several proteins are involved in NMD, such as Upf1, an essential protein that directly controls mRNA decay, and eIF5A, a eukaryotic initiation factor that is tightly associated with actively translated ribosomes and is an RNA-binding protein.

Currently, there are a number of compounds that are partially effective against NADs and function by suppressing nonsense codon recognition. While recent reports also indicate involvement of NMD in NADs and certain compounds that suppress NMD function, there is a need in the art for the further characterization of the NMD mechanism associated with various NADs. There also remains a need for compounds and methods that repress NMD and thereby significantly increase the level of NMD-susceptible mRNA, thereby potentially mitigating NAD symptoms. The instant invention addresses these needs.

SUMMARY OF THE INVENTION

The present invention relates to methods for treating a NAD comprising administering to a patient suffering from a NAD an inhibitor of NMD and a nonsense suppressor, whereby degradation of NMD susceptible mRNA is decreased and translation termination at a misplaced nonsense codon is blocked.

In one aspect of the invention, an inhibitor of NMD is a compound of formula (I):

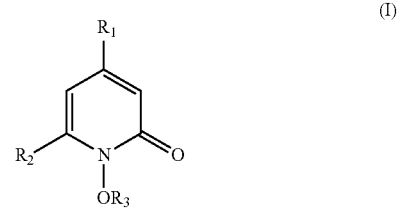

wherein
$R_1$ is $(C_1-C_6)$ alkyl;
$R_2$ is $(C_1-C_{10})$ straight or branched alkyl, $(C_3-C_6)$cycloalkyl or phenoxy$(C_1-C_3)$alkyl, where the phenoxy group is substituted by substituted or unsubstituted phenoxy; and
$R_3$ is hydrogen or a pharmacologically acceptable salt.

In yet another aspect, the inhibitor of NAD is a compound of the formula (II)

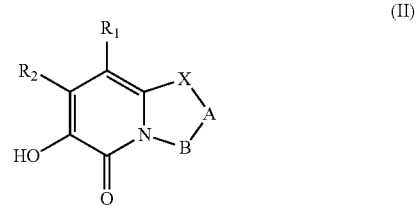

wherein
X is N, S, S=O, S(=O)$_2$ or $CR_3R_4$;
A and B are each independently $CR_5R_6$ or taken together are $CR_7=CR_8$;
$R_1$, $R_2$, $R_3$, $R_4$, $R_5$, and $R_6$, are each independently hydrogen, hydroxyl, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, $NR_9R_9$, amido, or alkoxycarbonyl;
$R_7$ and $R_8$ are each independently hydrogen, hydroxyl, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, NR₉R₉·, amido, or alkoxycarbonyl; or are taken together to form a substituted or unsubstituted aryl, heterocyclo or heteroaryl ring; and R₉ and R₉· are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, wherein groups that are substituted are independently substituted with one or more substituents selected from the group consisting of alkyl, alkenyl, alkynyl, cycloalkyl, aroyl, halo, haloalkyl, haloalkoxy, hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, aryloxy, alkanoyloxy, amino, alkylamino, arylamino, arylalkylamino, cycloalkylamino, heterocycloamino, mono- or disubstituted amino, alkanoylamino, aroylamino, aralkanoylamino, alkanoylamino, arylamino, aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido, nitro, cyano, carboxy, carbamyl, alkoxycarbonyl, guanidino or heterocyclo alkyl.

In another aspect, the inhibitor of NAD is a compound of formula (III) or (IV):

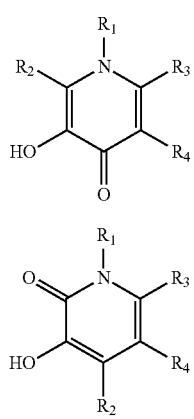

wherein R₁, R₂, R₃, and R₄ each individually represent a hydrogen, an alkyl, alkenyl, or alkoxy group containing 1 to about 8 carbon atoms, an aryl, arylaklyl, or cycloalkyl group containing about 5 to 12 carbon atoms, or a peptide or peptidomimetic moiety containing 10 to about 30 carbon atoms.

In another aspect, the present invention provides a pharmaceutical composition comprising a hydrazaline compound and at least a second inhibitor of NMD, each at a low concentration at which the hydrazaline compound or the second NMD inhibitor alone would not inhibit NMD. However, combination of the two components together can achieve effective inhibition, resulting in a synergistic effect.

In another aspect, the present invention provides use of combinations of NMD inhibitors, such as hydralazine or analogs and at least a structurally distinct additional NMD inhibitor, and a nonsense suppressor for treating a NAD or controlling expression of NAD causing proteins in cell culture.

In another aspect, the present invention provides use of combinations of NMD inhibitors, such as hydralazine or analogs and at least a structurally distinct additional NMD inhibitor, and a nonsense suppressor in the manufacture of a medicament for treating a NAD or controlling expression of NAD causing proteins in cell culture.

In one embodiment, the hydralazine compound can be combined with more than two, three, or four additional NMD inhibitors, each at a low non-inhibitory concentration against NMD but combined having a synergistic effect.

The hydralazine compound can be any compound in the hydralazine family known in the art that is an NMD inhibitor. Such a family of hydralazine compounds can be characterized by a general formula (V):

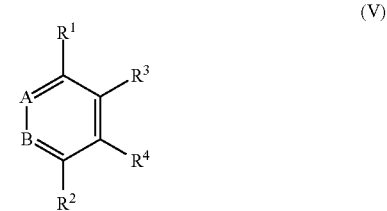

wherein A and B are independently nitrogen or substituted or unsubstituted carbon;

R¹ and R² are each independently hydrogen, hydrazine, hydrazone, or —CH₂COOH, provided that at least one of R¹ and R² is a hydrazine or hydrazone group;

at least one pair of R³ and R⁴, R¹ and R³, or R² and R⁴, together with the carbon atoms to which they are attached, form a 6-membered aromatic or non-aromatic ring fused onto the ring moiety comprising the A-B component through the two carbon atoms to which they are attached, wherein the rest of R¹, R², R³, and R⁴ are each independently selected from hydrogen, hydroxyl, halogen, C₁-C₄ alkyl, C₁-C₄ alkoxy, hydrazine, and hydrazone groups.

In yet another embodiment, the nonsense suppressor is selected from the group comprising an aminoglycoside antibiotic, a compound such as is disclosed in US Patent Application 20090203752 (J. A. Campbell et al.) or U.S. Pat. No. 7,449,570 (R. G. Wilde et al.), which are both hereby incorporated by reference in their entirety, and the like, or suppressor tRNA.

In one embodiment, the nonsense suppressor is Ataluren or analogs thereof, in particular, prodrug thereof, characterized by a structure of formula (VI):

wherein R is hydrogen (Ataluren), alkyl, aryl, arylalkyl, or the like.

In one embodiment, the nonsense suppressor is a compound of formula (VII):

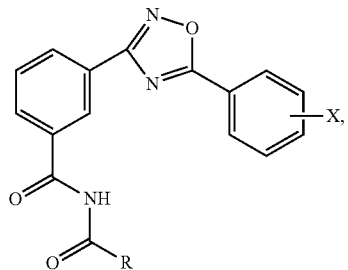

(VII)

or a pharmaceutically acceptable salt, solvate, or prodrug thereof, wherein:

X is a halogen;

R is selected from $C_1$-$C_8$ alkyl, $C_1$-$C_4$ haloalkyl, —$OR_1$, —$NHR^x$, and —$N(R^x)_2$ groups;

$R^1$ is $C_1$-$C_8$ alkyl group optionally substituted with one or more independently selected $R^a$ groups; a —$R^b$ group; pyrrolidinyl optionally substituted with one or more independently selected $C_1$-$C_4$ alkyl or oxo groups; piperidyl group optionally substituted with one or more independently selected $C_1$-$C_4$ alkyl groups, benzyl groups, or carboxy groups, which are in turn optionally substituted with one or more $C_1$-$C_4$ alkyl or $C_1$-$C_4$ alkoxy groups; tetrahydrofuryl group; tetrahydro-pyranyl group; tetrahydro-naphthyl group; or indanyl;

$R^x$, at each occurrence, is independently selected from hydrogen, $C_1$-$C_6$ alkyl, $C_1$-$C_4$ haloalkyl, $C_1$-$C_4$ alkoxy, $R^b$ group, pyrimidinyl, pyridyl, sulfonyl group optionally substituted with an —$R^b$ group; or alternatively two $R^x$ groups together with the nitrogen atom to which they are attached form a morpholinyl, pyrrolidinyl, isoindolinyl, or piperazinyl group, each optionally substituted by a phenyl group;

wherein $R^a$ is selected from halogen, $C_1$-$C_4$ alkoxy, carbamoyl optionally substituted with one or two independently selected $C_1$-$C_4$ alkyl or $C_1$-$C_4$ alkoxy groups, phosphinoyl group optionally substituted with one or two independently selected $C_1$-$C_4$ alkyl or $C_1$-$C_4$ alkoxy groups, morpholinyl group, pyridyl group, and $R^b$ group; and wherein $R^b$ is $C_6$-$C_{10}$ aryl optionally substituted with one or more substituents independently selected from hydroxyl, halogen, $C_1$-$C_4$ alkyl, $C_1$-$C_4$ haloalkyl, $C_1$-$C_4$ alkoxy, and amino group optionally substituted with one or more independently selected $C_1$-$C_4$ alkyl groups.

In one embodiment, the nonsense suppressor is a compound of formula (VII):

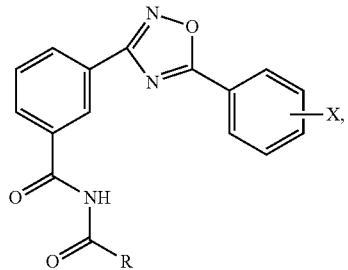

(VII)

wherein R is a $C_1$-$C_4$ alkyl group; a $C_1$-$C_4$ haloalkyl group; an —$OR^1$ group; or an amino group optionally substituted with one or two independently selected $R^x$ groups.

Examples of nonsense suppressors include, but are not limited to, those characterized by formula (VIII):

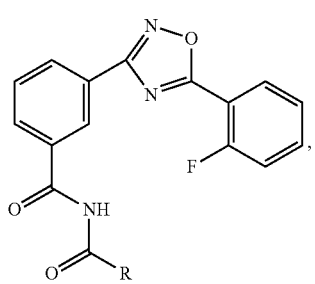

(VIII)

wherein R is $C_1$-$C_4$ alkyl, $C_1$-$C_4$ haloalkyl, —$OR^3$, —$NHR^x$, or —$N(R^x)_2$, wherein:

$R^3$ is $C_1$-$C_4$ alkyl, or $C_1$-$C_4$ haloalkyl, $C_6$-$C_{10}$ aryl, $C_3$-$C_8$ cycloalkyl, 5- to 10-membered heteroaryl, 5- to 10-membered heterocyclyl, $C_6$-$C_{10}$ aryl-($C_1$-$C_4$)alkyl, 5- to 10-membered heteroaryl-($C_1$-$C_4$)alkyl, 5- to 10-membered heterocyclyl-($C_1$-$C_4$)alkyl, each optionally substituted by one to five substituents independently selected from halogen, hydroxyl, $C_1$-$C_4$ alkyl, $C_1$-$C_4$ alkoxy, $C_1$-$C_4$ haloalkyl, and oxo; and wherein $R^x$, at each occurrence, is independently hydrogen, $C_1$-$C_4$ alkyl, or $C_1$-$C_4$ haloalkyl, $C_6$-$C_{10}$ aryl, $C_3$-$C_8$ cycloalkyl, 5- to 10-membered heteroaryl, 5- to 10-membered heterocyclyl, $C_6$-$C_{10}$ aryl-($C_1$-$C_4$)alkyl, 5- to 10-membered heteroaryl-($C_1$-$C_4$)alkyl, 5- to 10-membered heterocyclyl-($C_1$-$C_4$)alkyl, each optionally substituted by one to five substituents independently selected from halogen, hydroxyl, $C_1$-$C_4$ alkyl, $C_1$-$C_4$ alkoxy, $C_1$-$C_4$ haloalkyl, and oxo.

Specific examples of this type of compounds as nonsense suppressors include, but are not limited to, those listed in US 20090203752, which are incorporated herein by reference as if all the examples disclosed therein are hereby specifically listed.

A particularly preferred example in this class of compounds as nonsense suppressor has a formula:

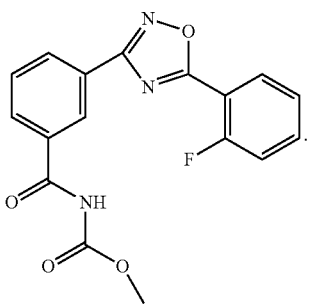

Any nucleoside compounds that can be used as nonsense suppressors can be used in the present invention, including but not limited to those described in U.S. Pat. No. 7,449,570 to Wilde et al. In particular, these compounds have a general structure of formula (IX):

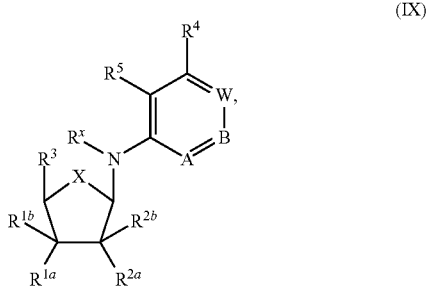

(IX)

or a pharmaceutically acceptable salt, solvate, or prodrug thereof, wherein:

X is O, S, or $CH_2$;

A, B and W are each independently N or $CR^6$, wherein $R^6$ is hydrogen, halogen, hydroxyl, $C_1$-$C_4$ alkoxy, $NR^aR^b$ cyano (—CN), or nitro (—$NO_2$);

$R^{1a}$, $R^{1b}$, $R^{2a}$, and $R^{2b}$ are each independently hydrogen, hydroxyl, $C_1$-$C_4$ alkoxy, halogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^1$ and $R^2$ taken together form a bond, or $R^1$ and $R^2$ taken together with the atoms to which they are attached form a substituted or unsubstituted heterocyclo, or $R^{1a}$ and $R^{1b}$ and/or $R^{2a}$ and $R^{2b}$ taken together with the carbon to which they are attached form C(=O);

$R^3$ is hydroxyl, substituted or unsubstituted alkyl, alkylcarboxy, arylcarboxy, amido, acyl, alkylcarbonyl, halogen, a biohydrolyzable group, —OP(O)$_3^{2-}$, —O[P(O)$_3$]$_2^{3-}$, —O[P(O)$_3$]$_3^{4-}$, —$N_3$, —$CH_2$—$NR^aN^b$ or —$CH_2$—$OR^x$;

$R^x$ is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, or substituted or unsubstituted heterocycloalkyl; and $R^4$ and $R^5$ are each independently hydrogen, hydroxy, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, $NR^aR^b$, amido, or alkoxycarbonyl;

$R^a$ and $R^b$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, or substituted or unsubstituted heterocycloalkyl, wherein groups that are substituted are independently substituted with one or more substituents selected from the group consisting of alkyl, alkenyl, alkynyl, cycloalkyl, aroyl, halo, haloalkyl, haloalkoxy, hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, aryloxy, alkanoyloxy, amino, alkylamino, arylamino, arylalkylamino, cycloalkylamino, heterocycloamino, mono- or di-substituted amino, alkanoylamino, aroylamino, aralkanoylamino, alkanoylamino, arylamino, aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamide, nitro, cyano, carboxy, carbamyl, alkoxycarbonyl, guanidino or heterocycloalkyl.

These and other aspects of the present invention will be better appreciated by reference to the following drawings and detailed description.

BRIEF DESCRIPTION OF THE DRAWINGS

FIG. 7]) with a nonsense suppressor, exemplified by G418, in this example used at 400 μM.

DETAILED DESCRIPTION OF THE INVENTION

Figure 1:
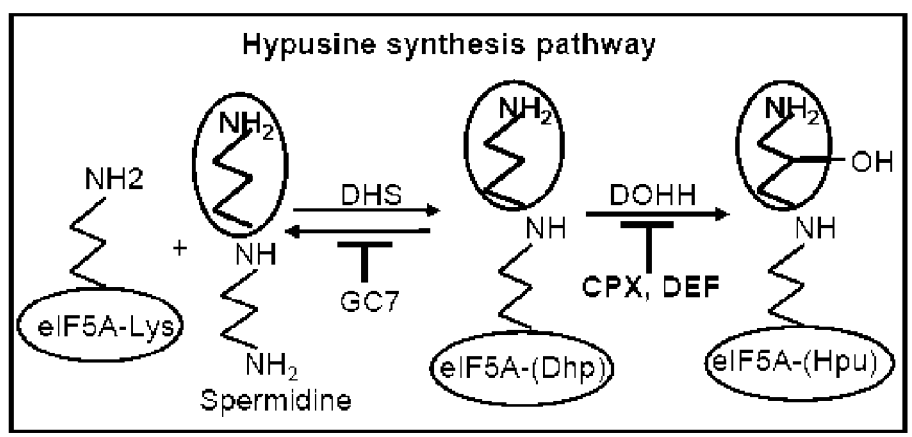
FIG. 1 illustrates the hypusine synthesis pathway of eIF5A.

As used herein, the following terms, unless otherwise indicated, shall be understood to have the following meaning:

"Biological agent" or "biological agents" include any agent known in the art such as, but not limited to, proteins or protein-based molecule, such as a mutant ligand, antibody, or the like, and nucleic acids or nucleic acid-based entities and the vectors used for their delivery.

"Compound" or "compounds" refers to conventional chemical compounds (e.g., small organic or inorganic molecules). To this end, the terms small molecule and compounds are interchangeable.

"Effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state.

"Nonsense-mediated decay" ("NMD") refers to a cellular mechanism that selectively degrades faulty messenger RNA ("mRNA") containing an out-of-place stop (nonsense) codon.

"Nonsense-associated disease" ("NAD") refers to a genetic disorder characterized by premature stop mutations that often lead to a complete loss of protein function and a severe reduction in mRNA levels due to NMD.

"NMD inhibitor" refers to a compound or any biological agent that decreases the activity of NMD in a cell and decreases the destruction of defective mRNA by any measurable amount, as compared to such a cell in the absence of such an inhibitor. NMD inhibitors may include, but are not limited, compounds that block DOHH activity.

"NAD inhibitor" refers to a compound or any biological agent that mitigates, inhibits, and/or prevents symptoms of a NAD.

A compound or agent is said to be "harmful to biological function" if it is harmful or otherwise damaging to a biological pathway. For example, as applied to the instant application, the prematurely terminated protein may be harmful to a biological function if it affects the relevant biological pathway, e.g., by competing with the normal protein or exerting a dominant negative effect. Prematurely terminated proteins which do not exert their normal function without actively interfering with the relevant biological pathway are not harmful to biological function.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

As used herein, with respect to administering an inhibitor, the terms "mitigate" or "mitigating" refers to reducing the progression and symptoms of a NAD. It may include executing a protocol, which may include administering one or more drugs to a patient (human or otherwise), in an effort to reduce signs or symptoms of the NAD.

As used herein, with respect to administering an inhibitor, the terms "prevent," or "preventing" refers to prophylactic treatment for halting a disease or condition. It may include executing a protocol, which may include administering one or more drugs to a patient (human or otherwise), in an effort to prevent signs or symptoms of the disease. In certain embodiments, prophylactic treatment prevents worsening of a disease or condition.

"Subject" refers to any animal (e.g., a mammal), including, but not limited to humans, non-human primates, rodents, and any other animal, which is to be the recipient of a particular treatment. Typically, the terms "subject" and "patient" are used interchangeably herein in reference to a human subject.

As used herein, with respect to administering an inhibitor, the terms "treat," "treating," or "treatment" refers to therapeutic treatment for halting or reducing a disease or condition. It may include executing a protocol, which may include administering one or more drugs to a patient (human or otherwise), in an effort to alleviate signs or symptoms of the disease. In certain embodiments, therapeutic treatment prevents worsening of a disease or condition.

As used herein, the term "patient" means an animal (e.g., cow, horse, sheep, pig, chicken, turkey, quail, cat, dog, mouse, rat, rabbit, guinea pig, etc.), preferably a mammal such as a nonprimate and a primate (e.g., monkey and human), most preferably a human In certain embodiments, the patient is an infant, child, adolescent or adult. In one embodiment, it has been determined through pre-screening that the patient possesses a non-sense mutation. In another embodiment, it has been determined through pre-screening which non-sense mutation the patient has (i.e., UAA, UGA, or UAG). In another embodiment, the patient is infected with bacterial cells (e.g., *Pseudomonas aeruginosa*). In another embodiment, the cells of the patient are virally infected. In another embodiment, the patient has a genetic mutation.

The present invention relates to methods of treating a NAD by preventing, mitigating, and/or inhibiting NMD. The present invention further relates to compounds and pharmaceutical compositions which are highly effective at preventing, mitigating, and/or inhibiting NMD. More specifically, the instant invention relates to preventing, mitigating, and/or inhibiting NMD by inhibiting the formation of the hypusine residue in cellular eIF5A precursor proteins.

Inhibition of NMD provides a mechanism to remediate an inherited disease by transcript stabilization, provided that the upstream nonsense codon is positioned such that the truncated protein has a beneficial biological effect. Likewise, inhibition of NMD provides a mechanism to remediate an acquired disease by transcript emergence, provided that the upstream nonsense codon is positioned such that the cryptic protein has a beneficial biological effect. Applicants have come to recognize that eIF5A is one protein involved in NMD, and that inhibition of eIF5A causes inhibition of the NMD pathway, thereby increasing the amount of NMD-susceptible mRNA, which results in the mitigation of NAD symptoms. In other cases, in which the truncated protein does not have a beneficial biological effect, inhibition of NMD leading to increased amount of the mRNA will be combined with stop codon suppression to cause production of full-length protein.

Approximately 33% of genetic and acquired diseases are NADs. The methods of the present invention relate to treating such NADs including, but not limited to, lysosomal disorders (e.g., Niemann-Pick disease), metabolism disorders (e.g., familial hypercholesterolemia and McArdle disease), familial cancer syndromes (e.g., retinoblastoma and breast cancer), neurodegenerative disorders (e.g., amyotrophic lateral sclerosis and spastic paraplegia), muscular disorders (congenital muscular dystrophy and autosomal recessive proximal spinal muscular atrophy), connective tissues disorders (Ehlers Danlos Syndrome), secretory disorders (e.g., cystic fibrosis), hematologic diseases (e.g., thalassemia), primary immunodeficiency disorders (e.g. ataxia-telangiectasia) and cardiovascular diseases (e.g., long QT syndrome and ischemia syndrome). Examples of other NADs include, but are not limited to, collagenopathies, frontotemporal dementia, Tay-Sachs disease, Parkinson disease, Smith-Lemli-Opitz syndrome, Alagille syndrome, Duchene's muscular Dystrophy, and Carney complex. Additionally, methods of the present invention also relate to treatment of various acquired diseases and infectious disorders (e.g., retrocyclin "reawakening" to curtail HIV transmission). Moreover, NMD is likely to be responsible for at least some cases of diverse diseases including cancer. Methods of the present invention apply to any disease resulting from decreased mRNA production or stability that could be treated.

In a further embodiment, the present invention relates to the treatment of NADs characterized by prematurely terminated proteins that are not harmful to biological functions.

In one embodiment, it is therapeutically sufficient to decrease the symptoms of a NAD by inhibition of NMD, thereby increasing the amount of protein generated from otherwise NMD susceptible mRNA. In other embodiments it is therapeutically sufficient to decrease the symptoms of a NAD by combination therapy in which NAD symptoms are decreased by both NMD inhibition and by suppressing nonsense codon recognition. Non-limiting examples of compounds capable of suppressing nonsense codon recognition are embodied by select aminoglycoside antibiotics (e.g. gentamicin) or the experimental agent PTC124 (Ataluren™). These compounds cause ribosome readthrough at the site of the nonsense stop codon in defective RNA, but are themselves either ineffective or inconsistently effective for treatment of NADs due to the efficient NMD-mediated destruction of defective RNA in at least a large subset of NAD relevant cells. However, if NMD-mediated destruction of defective RNA is rendered inefficient (e.g. by downregulation of NMD), readthrough-enhancing drugs cause synthesis of full-length protein and mitigation of symptoms in NADs.

Maturation of eIF5A involves both acetylation and hypusination and is necessary for most, if not all, of its biological roles. With reference to FIG. 1, hypusine is formed by the posttranslational modification of a specific lysine residue in both eIF5A isoforms. This modification of eIF5A entails two consecutive steps. In the first step, deoxyhypusine synthase ("DHS") catalyzes the cleavage of the polyamine spermidine and the transfer of its 3-aminobutyl moiety to the ε-amino group of lysine-50 of the eIF5A precursor, yielding a deoxyhypusine containing intermediate. In the second step, deoxyhypusine hydroxylase ("DOHH") hydroxylates the deoxyhypusyl-eIF5A intermediate to hypusine-containing mature eIF5A using molecular oxygen. The non-heme iron in the catalytic center of DOHH renders the enzyme susceptible to small molecule inhibitors that conform to the steric restrictions imposed by the active site pocket and interact with the metal via bidentate coordination.

In one embodiment, the present invention relates to therapeutic compositions and methods that employ compounds and compositions that inhibit the posttranslational formation of hypusine-containing mature eIF5A. With reference to FIG. 1, the inhibition of posttranslation formation of mature eIF5A is achieved by blocking either DHS or DOHH activity. For example, and not by way of limitation, Applicants have come to recognize that DHS activity is inhibited by GC7, and DOHH activity is inhibited by ciclopirox ("CPX") and deferiprone ("DEF"). Such inhibition suppresses NMD activity that contributes to NADs. The methods of the present invention involve administering, to eukaryotic cells, tissues, or individuals, compounds which block the posttranslational intracellular formation of hypusine, in an amount effective to suppress synthesis of bioactive eIF5A or its bioactive isoforms.

One embodiment of the present invention is a therapeutic composition or a pharmaceutical composition comprising a N-hydroxypyrid-2-one compound of formula (I) and derivatives thereof (including salts, solvates, and tautomeric forms):

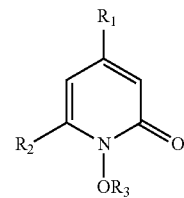

wherein
R$_1$ is (C$_1$-C$_6$) alkyl;
R$_2$ is (C$_1$-C$_{10}$) straight or branched alkyl, (C$_3$-C$_6$)cycloalkyl or phenoxy(C$_1$-C$_3$)alkyl, where the phenoxy group is substituted by substituted or unsubstituted phenoxy; and
R$_3$ is hydrogen or a pharmacologically acceptable salt.
Preferably, R$_1$ is methyl.
More preferably, R$_1$ is methyl, R$_2$ is cyclohexyl or

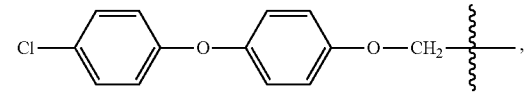

and R$_3$ is hydrogen.
In another embodiment, R$_1$ is methyl, R$_2$ is (CH$_3$)$_3$CCH$_2$(CH$_3$)CH$_2$— and R$_3$ is $_+$H$_3$NCH$_2$OH.
Examples of such compounds and salts thereof of formula (I) useful in the practice of the present invention include, but are not limited to, ciclopirox (CAS 29342-05-0), ribopirox (CAS 104153-37-9) and their analogs, such as metipirox (CAS 29342-02-7) or piroctone (CAS 506050-75-5); as well as their (1:1) ethanolamine salts, exemplified by octopirox (CAS 68890-6-4).

In one preferred embodiment, compounds of formula (I) comprise ciclopirox ("CPX") and its analogues:

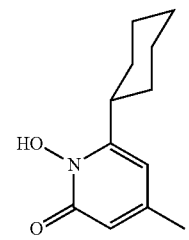

CPX is a topical antifungal (e.g., Batrafen™).
Another embodiment of the present invention is a therapeutic composition or a pharmaceutical composition comprising a compound of formula (II)

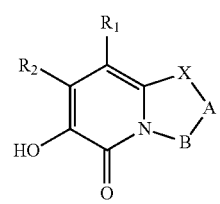

wherein

X is N, S, S=O, S(=O)$_2$ or CR$_3$R$_4$;

A and B are each independently CR$_5$R$_6$ or taken together are CR$_7$=CR$_8$;

R$_1$, R$_2$, R$_3$, R$_4$, R$_5$, and R$_6$, are each independently hydrogen, hydroxyl, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, NR$_9$R$_{9'}$, amido, or alkoxycarbonyl;

R$_7$ and R$_8$ are each independently hydrogen, hydroxyl, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, NR$_9$R$_{9'}$, amido, or alkoxycarbonyl; or are taken together to form a substituted or unsubstituted aryl, heterocyclo or heteroaryl ring; and R$_9$ and R$_{9'}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, wherein groups that are substituted are independently substituted with one or more substituents selected from the group consisting of alkyl, alkenyl, alkynyl, cycloalkyl, aroyl, halo, haloalkyl, haloalkoxy, hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, aryloxy, alkanoyloxy, amino, alkylamino, arylamino, arylalkylamino, cycloalkylamino, heterocycloamino, mono- or disubstituted amino, alkanoylamino, aroylamino, aralkanoylamino, alkanoylamino, arylamino, aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido, nitro, cyano, carboxy, carbamyl, alkoxycarbonyl, guanidino or heterocycloalkyl.

In one embodiment of the invention, X is O, S or S(=O)$_2$, R$_1$ is hydrogen or pyridyl, R$_2$ is hydrogen, A is CH$_2$ when B is CH$_2$ or CHCO$_2$Me or taken together, A and B form a phenyl ring. Preferred compounds include those where X is O, R$_1$ is hydrogen, A is CH$_2$ and B is CHCO$_2$Me; X is S, R$_1$ is hydrogen, A is CH$_2$ and B is CHCO$_2$Me; X is S(=O)$_2$, R$_1$ is hydrogen, A is CH$_2$ and B is CHCO$_2$Me; X is S, R$_1$ is hydrogen, A is CH$_2$ and B is CH$_2$; X is S, R$_1$ is pyridyl, A is CH$_2$ and B is CH$_2$; or X is S, R$_1$ is hydrogen, A and B form a phenyl ring.

Another embodiment of the present invention is a therapeutic composition or a pharmaceutical composition comprising a compound of formula (III) or (IV):

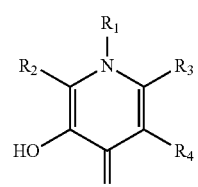

(III)

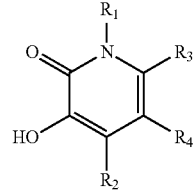

(IV)

wherein R$_1$, R$_2$, R$_3$, and R$_4$ each individually represent a hydrogen, an alkyl, alkenyl or alkoxy group containing 1 to about 8 carbon atoms, an aryl, arylalkyl, cycloalkyl group containing about 5 to 12 carbon atoms, or a carboalkoxy or carbamyl group containing up to 8 carbon atoms, or a peptide or peptidomimetic moiety containing 10 to about 30 carbon atoms.

In a preferred embodiment, compounds of formula (III) and (IV) comprise deferiprone ("DEF") and its analogues:

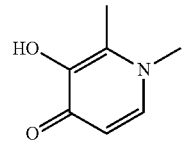

DEF is a medicinal chelator (e.g., Ferriprox™) taken orally for systemic iron overload.

These compounds may be made by the methods disclosed in U.S. Pat. No. 2,540,218 and U.S. Pat. No. 4,797,409, the contents of which are incorporated herein by reference in their entirety.

The hydroxypyridones of the present invention may be used in the free form or as their physiologically tolerated salts with inorganic or organic bases, such as, but not limited to, NaOH, KOH, Ca(OH)$_2$, NH$_3$, and H$_2$NCH$_2$CH$_2$OH.

In another aspect, the present invention provides a pharmaceutical composition comprising a hydrazaline compound and at least a second inhibitor of NMD, each at a low concentration at which the hydrazaline compound or the second NMD inhibitor alone would not inhibit NMD. However, combination of the two components together can achieve effective inhibition, resulting in a synergistic effect.

In another aspect, the present invention provides use of combinations of NMD inhibitors, such as hydralazine or analogs and at least a structurally distinct additional NMD inhibitor, and a nonsense suppressor for treating a NAD or controlling expression of NAD causing proteins in cell culture.

In another aspect, the present invention provides use of combinations of NMD inhibitors, such as hydralazine or analogs and at least a structurally distinct additional NMD inhibitor, and a nonsense suppressor in the manufacture of a medicament for treating a NAD or controlling expression of NAD causing proteins in cell culture.

In another embodiment, the hydralazine compound can be combined with more than two, three, or four additional NMD inhibitors, each at a low non-inhibitory concentration against NMD but combined having a synergistic effect.

The hydralazine compound can be any compound in the hydralazine family known in the art that is an NMD inhibitor. Such a family of hydralazine compounds can be characterized by a general formula (V):

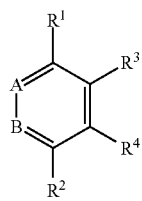

(V)

wherein A and B are independently nitrogen or substituted or unsubstituted carbon;

$R^1$ and $R^2$ are each independently hydrogen, hydrazine, hydrazone, or —$CH_2COOH$, provided that at least one of $R^1$ and $R^2$ is a hydrazine or hydrazone group;

at least one pair of $R^3$ and $R^4$, $R^1$ and $R^3$, or $R^2$ and $R^4$, together with the carbon atoms to which they are attached, form a 6-membered aromatic or non-aromatic ring fused onto the ring moiety comprising the A-B component through the two carbon atoms to which they are attached, wherein the rest of $R^1$, $R^2$, $R^3$, and $R^4$ are each independently selected from hydrogen, hydroxyl, halogen, $C_1$-$C_4$ alkyl, $C_1$-$C_4$ alkoxy, hydrazine, and hydrazone groups.

The term "hydrazine group", as used herein, refers to "—$NHNHR^a$" wherein $R^a$ is hydrogen or any substituent, preferably biohydrolyzable protecting group, including but not limited to acyl groups, such as acetyl, formyl, benzoyl, or the like.

The term "hydrazone group", as used herein, refers to "=N—$NHR^a$" or "—NH—N=$CR^xR^y$", wherein $R^a$ is hydrogen or any substituent, preferably biohydrolyzable protecting group, including but not limited to acyl groups, such as acetyl, formyl, benzoyl, or the like, and wherein $R^x$ and $R^y$ can be hydrogen or any substituents, including but not limited to optionally substituted alkyl, alkenyl, aryl, heteroaryl, cycloalkyl, heterocyclyl, arylalkyl, cycloalkylalkyl, heteroarylaryl, heterocyclylalkyl, or the like.

In a preferred embodiment, the fused ring by $R^3$ and $R^4$, $R^1$ and $R^3$, or $R^2$ and $R^4$ pair is a benzene ring, a cyclohexane ring, or a 6-membered heterocycle comprising one, two or three heteroatoms independently selected from O, S, and N, wherein the fused ring system is optionally substituted by one, two, three, or four substituents independently selected from halogen, hydroxyl, $C_1$-$C_4$ alkyl, $C_1$-$C_4$ alkoxy, and acyl.

In a more preferred embodiment, the hydralazine compound of NMD inhibitor is selected from the group consisting of:

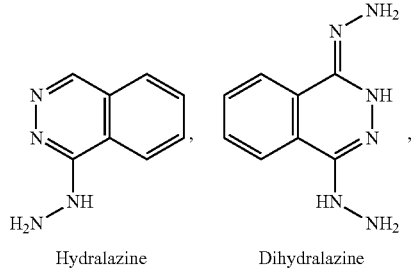

Hydralazine          Dihydralazine

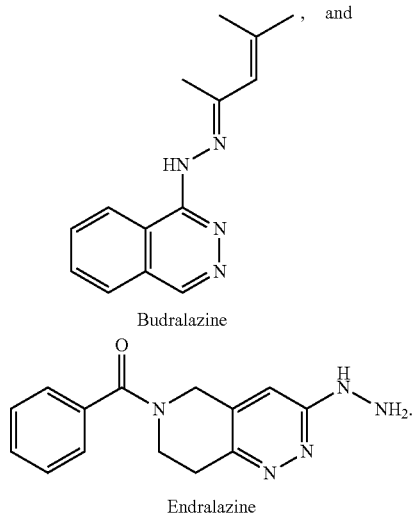

Budralazine

Endralazine

In yet another embodiment, the nonsense suppressor is selected from the group comprising an aminoglycoside antibiotic, a compound such as is disclosed in US Patent Application 20090203752 (J. A. Campbell et al.) or U.S. Pat. No. 7,449,570 (R. G. Wilde et al.), which are both hereby incorporated by reference in their entirety, and the like, or suppressor tRNA.

In one embodiment, the nonsense suppressor is Ataluren or analogs thereof, in particular prodrugs thereof, characterized by a structure of formula (VI):

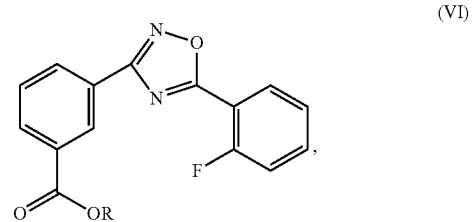

(VI)

wherein R is hydrogen (Ataluren), alkyl, aryl, arylalkyl, or the like.

In one embodiment, the nonsense suppressor is a compound of formula (VII):

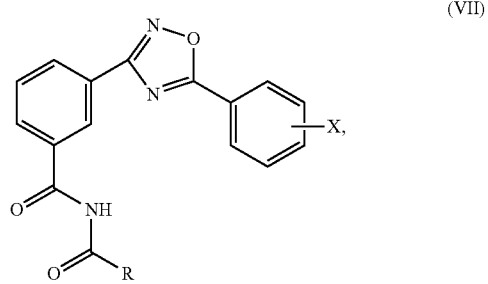

(VII)

or a pharmaceutically acceptable salt, solvate, or prodrug thereof, wherein:

X is a halogen;

R is selected from $C_1$-$C_8$ alkyl, $C_1$-$C_4$ haloalkyl, —$OR_1$, —$NHR^x$, and —$N(R^x)_2$ groups;

R[1] is C$_1$-C$_8$ alkyl group optionally substituted with one or more independently selected R$^a$ groups; a —R$^b$ group; pyrrolidinyl optionally substituted with one or more independently selected C$_1$-C$_4$ alkyl or oxo groups; piperidyl group optionally substituted with one or more independently selected C$_1$-C$_4$ alkyl groups, benzyl groups, or carboxy groups, which are in turn optionally substituted with one or more C$_1$-C$_4$ alkyl or C$_1$-C$_4$ alkoxy groups; tetrahydrofuryl group; tetrahydro-pyranyl group; tetrahydro-naphthyl group; or indanyl;

R$^x$, at each occurrence, is independently selected from hydrogen, C$_1$-C$_6$ alkyl, C$_1$-C$_4$ haloalkyl, C$_1$-C$_4$ alkoxy, R$^b$ group, pyrimidinyl, pyridyl, sulfonyl group optionally substituted with an —R$^b$ group; or alternatively two R$^x$ groups together with the nitrogen atom to which they are attached form a morpholinyl, pyrrolidinyl, isoindolinyl, or piperazinyl group, each optionally substituted by a phenyl group;

wherein R$^a$ is selected from halogen, C$_1$-C$_4$ alkoxy, carbamoyl optionally substituted with one or two independently selected C$_1$-C$_4$ alkyl or C$_1$-C$_4$ alkoxy groups, phosphinoyl group optionally substituted with one or two independently selected C$_1$-C$_4$ alkyl or C$_1$-C$_4$ alkoxy groups, morpholinyl group, pyridyl group, and R$^b$ group; and wherein R$^b$ is C$_6$-C$_{10}$ aryl optionally substituted with one or more substituents independently selected from hydroxyl, halogen, C$_1$-C$_4$ alkyl, C$_1$-C$_4$ haloalkyl, C$_1$-C$_4$ alkoxy, and amino group optionally substituted with one or more independently selected C$_1$-C$_4$ alkyl groups.

In one embodiment, the nonsense suppressor is a compound of formula (VII):

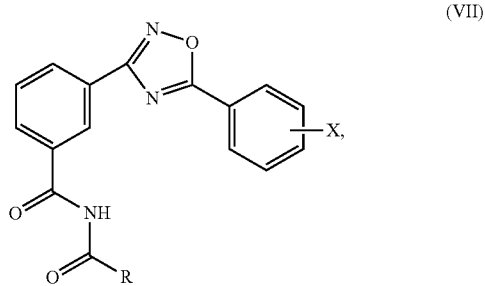

(VII)

wherein R is a C$_1$-C$_4$ alkyl group; a C$_1$-C$_4$ haloalkyl group; an —OR$^1$ group; or an amino group optionally substituted with one or two independently selected R$^x$ groups.

Examples of nonsense suppressors include, but are not limited to, those characterized by formula (VIII),

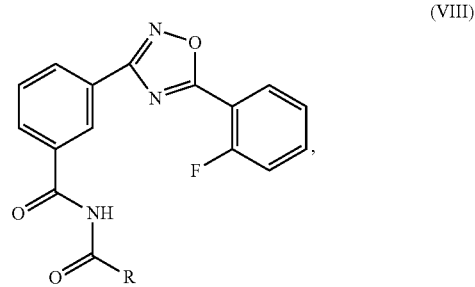

(VIII)

where in R is C$_1$-C$_4$ alkyl, C$_1$-C$_4$ haloalkyl, —OR$_3$, —NHR$^x$, or —N(R$^x$)$_2$, wherein:

R$^3$ is C$_1$-C$_4$ alkyl, or C$_1$-C$_4$ haloalkyl, C$_6$-C$_{10}$ aryl, C$_3$-C$_8$ cycloalkyl, 5- to 10-membered heteroaryl, 5- to 10-membered heterocyclyl, C$_6$-C$_{10}$ aryl-(C$_1$-C$_4$)alkyl, 5- to 10-membered heteroaryl-(C$_1$-C$_4$)alkyl, 5- to 10-membered heterocyclyl-(C$_1$-C$_4$)alkyl, each optionally substituted by one to five substituents independently selected from halogen, hydroxyl, C$_1$-C$_4$ alkyl, C$_1$-C$_4$ alkoxy, C$_1$-C$_4$ haloalkyl, and oxo; and wherein R$^x$, at each occurrence, is independently hydrogen, C$_1$-C$_4$ alkyl, or C$_1$-C$_4$ haloalkyl, C$_6$-C$_{10}$ aryl, C$_3$-C$_8$ cycloalkyl, 5- to 10-membered heteroaryl, 5- to 10-membered heterocyclyl, C$_6$-C$_{10}$ aryl-(C$_1$-C$_4$)alkyl, 5- to 10-membered heteroaryl-(C$_1$-C$_4$)alkyl, 5- to 10-membered heterocyclyl-(C$_1$-C$_4$)alkyl, each optionally substituted by one to five substituents independently selected from halogen, hydroxyl, C$_1$-C$_4$ alkyl, C$_1$-C$_4$ alkoxy, C$_1$-C$_4$ haloalkyl, and oxo.

Specific examples of this type of compounds as nonsense suppressors include, but are not limited to, those listed in US 20090203752, which are incorporated herein by reference as if all the examples disclosed therein are hereby specifically listed.

A particularly preferred example in this class of compounds as nonsense suppressor has a formula:

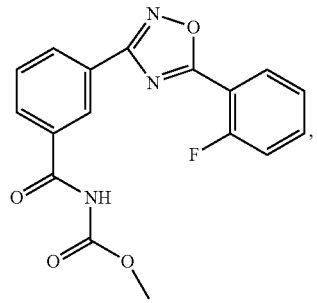 [SMILES: COC(=O)NC(=O)c1cccc(-c2noc(-c3ccccc3F)n2)c1]

Any nucleoside compounds that can be used as nonsense suppressors can be used in the present invention, including but not limited to those described in U.S. Pat. No. 7,449,570 to Wilde et al. In particular, these compounds have a general structure of formula (IX):

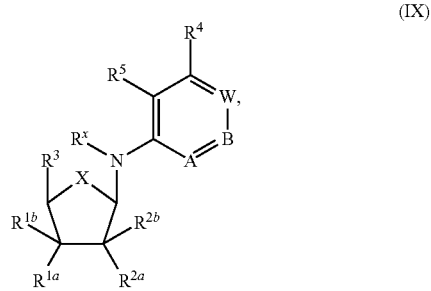

(IX)

or a pharmaceutically acceptable salt, solvate, or prodrug thereof, wherein:

X is O, S, or CH$_2$;

A, B and W are each independently N or CR$^6$, wherein R$^6$ is hydrogen, halogen, hydroxyl, C$_1$-C$_4$ alkoxy, NR$^a$R$^b$, cyano (—CN), or nitro (—NO$_2$);

R$^{1a}$, R$^{1b}$, R$^{2a}$ and R$^{2b}$ are each independently hydrogen, hydroxyl, C$_1$-C$_4$ alkoxy, halogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^1$ and $R^2$ taken together form a bond, or $R^1$ and $R^2$ taken together with the atoms to which they are attached form a substituted or unsubstituted heterocyclo, or $R^{1a}$ and $R^{1b}$ and/or $R^{2a}$ and $R^{2b}$ taken together with the carbon to which they are attached form C(=O);

$R^3$ is hydroxyl, substituted or unsubstituted alkyl, alkylcarboxy, arylcarboxy, amido, acyl, alkylcarbonyl, halogen, a biohydrolyzable group, —OP(O)$_3^{2-}$, —O[P(O)$_3$]$_2^{3-}$, —O[P(O)$_3$]$_3^{4-}$, —N$_3$, —CH$_2$—NR$^a$N$^b$ or —CH$_2$—OR$^x$;

$R^x$ is hydrogen, substituted or unsubstituted alkyl, substituted or unsubstituted aryl, substituted or unsubstituted heteroaryl substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl; and $R^4$ and $R^5$ are each independently hydrogen, hydroxy, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroaryl alkyl, substituted or unsubstituted cycloalkylalkyl, substituted or unsubstituted heterocycloalkyl, alkoxy, alkylthioether, carboxyalkyl, carbonylalkyl, amino, NR$^a$R$^b$, amido, or alkoxycarbonyl;

R$^a$ and R$^b$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, wherein groups that are substituted are independently substituted with one or more substituents selected from the group consisting of alkyl, alkenyl, alkynyl, cycloalkyl, aroyl, halo, haloalkyl, haloalkoxy, hydroxy, alkoxy, alkylthioether, cycloalkyloxy, heterocylooxy, oxo, alkanoyl, aryl, arylalkyl, alkylaryl heteroaryl, heteroarylalkyl, alkylheteroaryl, aryloxy, alkanoyloxy, amino, alkylamino, arylamino, arylalkylamino, cycloalkylamino, heterocycloamino, mono- or di-substituted amino, alkanoylamino, aroylamino, aralkanoylamino, alkanoylamino, arylamino, aralkanoylamino, thiol, alkylthio, arylthio, arylalkyl thio, cycloalkylthio, heterocyclothio, alkylthiono, arylthiono, arylalkylthiono, alkylsulfonyl, arylsulfonyl, arylalkylsulfonyl, sulfonamido, nitro, cyano, carboxy, carbamyl, alkoxycarbonyl, guanidino or heterocycloalkyl.

Specific examples of nucleosides as nonsense suppressors include, but are not limited to, those listed in U.S. Pat. No. 7,449,570, which are incorporated herein by reference as if all the examples disclosed therein are hereby specifically listed. A preferred compound of this type is Clitocine:

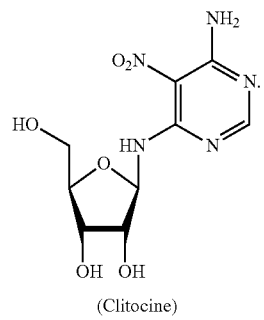

(Clitocine)

In yet another embodiment, the nonsense suppressor is selected from the group comprising an aminoglycoside antibiotic, a compound such as is disclosed in US Patent Application 20090203752 or U.S. Pat. No. 7,449,570 and the like, or suppressor tRNA. Examples of aminoglycoside antibiotics include Amikacin (Amikin), Gentamicin (Garamycin), G-Mycin, Jenamicin, Kanamycin (Kantrex), Neomycin (Mycifradin, Myciguent), Netilmicin (Netromycin), Paromomycin, Streptomycin, Tobramycin (Nebcin) and the like. An exemplary compound of U.S. Pat. No. 7,449,570 is Clitocine. An exemplary compound of US Application 20090203752 is PTC124 (Ataluren).

For purposes of the present inventive methods, the amount or dose of the compound administered should be sufficient to affect a therapeutic response in the animal over a reasonable time frame. Particularly, the dose of any composition including one or more of the compounds of any of formula (I)-(IV) should be sufficient to inhibit formation of hypusine in the precursor protein of eIF5A within about 24 hours. The dose will be determined by the efficacy of the particular compound and the condition of the patient, tissue, or cell sample as well as the mass of the sample or patient to be treated. Many assays for determining an administered dose are known in the art.

For purposes of the present invention, an assay which comprises comparing the extent to which disruption of the NMD pathway increases gene expression can be used to determine a starting dose to be administered. Depletion of eIF5A by RNA silencing inhibits NMD, resulting in an increase in gene expression of NMD sensitive constructs. Such assays measure expression from constructs that carry 3' signals known to confer NMD sensitivity or insensitivity. Those constructs that are sensitive to NMD generate approximately 5-fold less mRNA. Expression from the NMD-sensitive constructs is boosted by administration of compounds that inhibit hypusination of eIF5A. In a preferred embodiment, methods of the present invention are directed to inhibition of eIF5A hypusination by compounds of formula (I)-(IV), preferably ciclopirox and deferiprone. Both ciclopirox and deferiprone are iron chelators.

In other embodiments, the method for treating a NAD comprises administering to a patient suffering from a NAD a composition comprising an RNA interference therapy agent capable of inhibiting at least one of eIF5A, DOHH or DHS.

The RNA interfering agent may be an antisense nucleotide, siRNA, shRNA, or a DNA construct (e.g., a plasmid or a vector) encoding same.

siRNAs are double stranded RNA agents that have complementary to (i.e., able to basepair with) a portion of the target mRNA. shRNA molecules are basically siRNA molecules wherein the two strands are connected by a loop thereby resulting in a formation of a hairpin-like structure. Generally, complementarity to the target is 100%, but can be less if desired, such as 91%, 92%, 93%, 94%, 95%, 96%, 97%, 98%, or 99%. For example, 19 bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences.

The small interfering RNA sequence needs to be of sufficient length to bring the small interfering RNA and target RNA together through complementary base-pairing interactions. The small interfering RNA of the invention may be of varying lengths. The length of the small interfering RNA is preferably greater than or equal to ten nucleotides and of sufficient length to stably interact with the target RNA; specifically 15-30 nucleotides; more specifically any integer between 15 and 30 nucleotides, such as 15, 16, 17, 18, 19, 20, 21, 22, 23, 24, 25, 26, 27, 28, 29, and 30.

A person of ordinary skill in the art would be able to select an active RNA interfering agent based on the facts that sequences for eIF5A, DOHH and DHS are well known in the art and available from public databases and that criteria for selection of active RNA interference agents are known in the art.

For example, US Publication 20070031844 by Khvorova et al. or US Publication 20060275762 by Saigo et al. In other embodiments, siRNAs or antisense oligonucleotides may be used to inhibit the expression of enzymes DOHH and/or DHS that modulate the activity of eIF5A. In contrast, regions having high G-C content are usually not good candidates for antisense oligonucleotides.

The nucleic acid sequence encoding the active antisense, siRNA, or shRNA may be incorporated within a vector, preferably, a viral vector. Suitable vectors include, without limitations, adeno-associated viral vector, retroviral vectors, or adenoviral vectors. The methods of subcloning the sequences encoding the active RNA interference agents are also well known in the art.

Furthermore, all of the present inventive methods can comprise the administration of the compound, in the presence or absence of an agent that enhances its efficacy, or the methods can further comprise the administration of other suitable components, such as compounds that suppress nonsense codon recognition. Such suppression reduces the efficiency of translation termination at the misplaced nonsense mutations by administering certain pharmacological compounds or suppressor tRNAs. Examples of suppressor tRNAs and other pharmacological compounds that suppress nonsense mutations should be readily apparent to one skilled in the art.

One of ordinary skill in the art will readily appreciate that each compound of the present inventive methods can be modified in any number of ways, such that the therapeutic efficacy of the compound is increased through the modification. For instance, the compound could be conjugated either directly or indirectly through a linker to a targeting moiety. The practice of conjugating compounds to targeting moieties is known in the art. See, e.g., Wada et al, J. Drug Targeting, 3:111 (1995); U.S. Pat. No. 5,087,616; and U.S. Pat. No. 5,849,587, the contents of which are incorporated herein by reference in their entirety. The term "targeting moiety" as used herein, refers to any molecule or agent that specifically recognizes and binds to a cell surface receptor, such that the targeting moiety directs the delivery of the compound to a population of cells on which surface the receptor is expressed. Targeting moieties include, but are not limited to, antibodies, or fragments thereof, peptides, hormones, growth factors, cytokines, and any other naturally or non-naturally existing ligands, which bind to cell surface receptors. The term "linker" as used herein, refers to any agent or molecule that bridges the compound to the targeting moiety.

One of ordinary skill in the art recognizes that sites on the compounds, which are not necessary for the function of the compound, are ideal sites for attaching a linker and/or a targeting moiety, provided that the linker and/or targeting moiety, once attached to the compound does not interfere with the function of the compound, i.e., the ability to inhibit formation of the hypusine residue and form eIF5A.

One skilled in the art will appreciate that suitable methods of administering a compound of the present invention are known, and, although more than one route can be used to administer a particular composition, a particular route can provide a more immediate and more effective response than another route.

In the practice of the present invention, compositions that include compounds of formula (I)-(IV) can be administered topically or systemically (intravenously or subcutaneously). More particularly, such administration can be orally; parenterally, i.e., by subcutaneous, intravascular, or intramuscular injection; intraperitoneally; intrathecally; or by topical application, e.g., to skin or eyes, or by application to the mucous membranes of the nose, throat, bronchial tree, genital tract, or rectum, and so forth. They may be administered alone or with suitable pharmaceutical carriers, and can be in solid or liquid form such as tablets, capsules, powders, solutions, suspensions, or emulsions.

The size of the dosage of the compound of the present invention will also be determined by the existence, nature and extent of any adverse side effects that might accompany the administration of a particular compound. Ultimately, the attending physician will decide the dosage of the compound of the present invention with which to treat each individual patient, taking into consideration a variety of factors, such as age, body weight, general health, diet, sex, inhibitor to be administered, route of administration, and the severity of the condition being treated.

Formulations suitable for oral administration of compositions which include compounds of the present invention can consist of (a) liquid solutions, such as an effective amount of the compounds dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch potato starch, microcrystalline cellulose, acacia, gelatin, colloidal silicon dioxide, croscarmellose, sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Formulations of the compounds of formula (I)-(IV) in compositions suitable for parenteral administration (subcutaneous, intravascular, or intramuscular injection) include aqueous and non-aqueous solutions, isotonic sterile injection solutions, which can contain antioxidants, buffers, bacteriostats, and solutes that render the formulation isotonic with the blood of the intended recipient, and aqueous and non-aqueous solutions, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described. In general, water, saline, aqueous dextrose and related sugar solution, and glycols such as propylene glycol or polyethylene glycol, are preferred liquid carriers, particularly for injectable solutions.

The pharmaceutical products of the present invention are prepared by dissolving, mixing, granulating, or tablet-coating processes known to those skilled in the art. For oral administration, the active compounds or their physiologically tolerated derivatives such as salts, esters, or amides, are mixed with the additives customary for this purpose, such as vehicles, stabilizers, or inert diluents, and are converted by customary methods into a suitable form for administration, such as tablets, coated tablets, hard or soft gelatin capsules, aqueous, alcoholic, or oily suspensions, or aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant like stearic acid or magnesium stearate. Examples of suitable oily vehicles or solvents are vegetable or animal oils, such as sunflower oil or fish-liver oil. Preparations can be effected both as dry and as wet granules.

For use as aerosols, the active compounds or their physiologically tolerated derivatives such as salts, esters, or amides, may be dissolved or suspended in a physiologically acceptable liquid and packaged in a pressurized aerosol container together with suitable propellants, for example, hydrocarbon propellants like propane, butane, or isobutane with conventional adjuvants. The agents which block intracellular hypusine formation, in accordance with the present invention, may also be administered from a non-pressurized container such as a nebulizer or atomizer.

For topical administration to external or internal body surfaces, e.g., in the form of creams, gels, or drops, and so forth, the active compounds or their physiologically tolerated derivatives such as, salts, esters, or amides, are prepared and applied as solutions, suspensions, or emulsions in a physiologically acceptable diluent with or without a pharmaceutical carrier.

Diagnostics of nonsense mutations is complicated due to NMD which removes the defective mRNA. However, once NMD is inhibited, e.g., by inhibition of eIF5A, the relative number of defective mRNA templates is increased. As a result, signal-to-noise ratio is also increased thus allowing for a more reliable detection of such nonsense-mutated mRNA and thus for actionable diagnostic information.

Accordingly, in one embodiment, the method comprises obtaining a cell sample from a patient, treating said sample with an inhibitor of eIF5A, preferably culturing said cells under time and conditions sufficient to express nonsense mRNA encoding a prematurely truncated protein, extracting said mRNA, preparing a cDNA from said mRNA, and analyzing the resulting cDNA, e.g., by restriction analysis or by sequencing.

According to this aspect, the cell sample should comprise cells where the mRNA containing premature stop codon is expressed, and therefore, the nature of the cell sample would ultimately depend on the nature of the mRNA which is to be tested. The means for inhibiting eIF5A are also known in the art and/or discussed in the instant specification. For example, in certain embodiments, eIF5A may be inhibited using the compounds according to the Formulae IIV, with the limitations for the side chain substitutions as described above.

In other embodiments, RNAi agents may be used, such as antisense nucleotides and/or siRNA (or shRNA). As noted above, the sequences for the suitable targets (eIF5A, DOHH and DHS) are well known in the art, and the algorithms for selecting suitable RNA I agents are also described in the prior art. Similarly, the methods of culturing cells, extracting mRNA, and obtaining cDNA from mRNA are well known and do not need to be described in details herein.

The following non-limiting examples set forth below illustrate certain aspects of the invention. These examples are illustrative only, and are not intended to limit the remainder of the disclosure in any way.

EXAMPLES

Example 1: Prevention of Maturation of eIF5A by Inhibition of DOHH

To examine the effect of compounds on the synthesis of modified eIF5A, 293T cells transfected with a FLAG-tagged eIF5A expression vector were simultaneously treated with ciclopirox ("CPX") or deferiprone ("DEF").

FLAG-eIF5A was monitored using NIH-353 and anti-FLAG antibodies (FIGS. 2A and 2B). FIG. 2A illustrates inhibition of eIF5A modification in 293T cells. Cells transfected with FLAG-tagged eIF5A were untreated or treated with increasing concentrations of CPX as indicated, or with agent P2. FIG. 2B illustrates cells transfected with FLAG-tagged eIF5A that were untreated or treated with increasing concentrations of DEF as indicated, or with DFOX. At 24 hours post-transfection, whole cell extract ("WCE") was analyzed by immunoblotting with the NIH-353 anti-eIF5A antibody (upper panel) and anti-actin antibody (lower panel). The NIH-335 antibody reacts preferentially with post-translationally modified eIF5A. CPX reduced the appearance of mature eIF5A over the 3-30 µM concentration range, while DEF was effective at 200-400 µM. The compounds did not alter the expression of actin. Comparable results have been obtained in other cell types by spermidine labeling of eIF5A. In addition to the CPX homolog Agent P2, deferoxamine ("DFOX"; Desferal™) was used as a control compound. DFOX, a metal-binding hydroxamate like CPX and Agent P2 (FIG. 3), is a globally used medicinal iron chelator. Referring to FIGS. 2A and 2B, in contrast to CPX and DEF, P2 and DFOX had little or no effect on the appearance of mature FLAG-eIF5A (FIGS. 2A and 2B), indicating that the ability to chelate iron is insufficient to inhibit DOHH and the maturation of eIF5A.

FIG. 2C illustrates cells transfected with FLAG-tagged eIF5A that were treated with CPX (30 µM), P2 (30 µM), DEF (250 µM), DFOX (10 µM), or no compound (-). At 24 hours post transfection, WCE was analyzed by immunoblotting with the NIH-353 anti-eIF5A antibody (upper panel) and anti-FLAG antibody (lower panel). The control culture was transfected with empty vector and no compound was added. None of these compounds reduced the overall expression of the FLAG-eIF5A protein detectably (FIG. 2C), ruling out general inhibitory effects on gene expression. Based on these results, 30 μM CPX and 250 μM DEF were used for subsequent experiments.

These results indicate that eIF5A forms tight complexes with its modifying enzymes. Unmodified eIF5A (lysine-50) immunoprecipitates with DHS, and deoxyhypusyl-eIF5A interacts with DOHH in vitro. The deoxyhypusyl-eIF5A:DOHH complex formed in vivo can be detected by immunoprecipitation from cell extracts. Taking advantage of this finding, the effects of the compounds on the enzyme-substrate interaction was tested, the results of which are illustrated in FIG. 2D. FLAG-eIF5A was expressed in 293T cells. 293T cells transfected with FLAG-eIF5A were untreated (-) or treated with GC7 (10 μM) or CPX (30 μM), P2 (30 μM), DEF (250 μM), or DFOX (10 μM). WCE prepared at 24 hours post-transfection was immunoprecipitated with anti-FLAG antibody. Complexes that immunoprecipitated with anti-FLAG antibody were immunoblotted and probed with antibodies against DOHH. Endogenous DOHH co-immunoprecipitated with FLAG-eIF5A, and this association was largely prevented by treatment with CPX or DEF (FIG. 2D, top panel). Consistent with their inability to inhibit eIF5A maturation, neither P2 or DFOX prevented the formation of the eIF5A:DOHH complex. As a further control, the DHS inhibitor GC7 was included in this assay. No DOHH was associated with FLAG-eIF5A in the presence of GC7 because it prevents the synthesis of deoxyhypusyl-eIF5A. As expected, none of the compounds affected the immunoprecipitation of FLAG-eIF5A (FIG. 2D, middle panel; note that the band marked with an asterisk (*) is background due to IgG light chain) or the expression of endogenous eIF5A (FIG. 2D, bottom panel).

FIG. 2E illustrates 293T cells transfected with FLAG-DHS, FLAG-DOHH or empty vector (control) were treated with GC7, CPX, or DEF, or no drug (-) at the same concentration as in FIG. 2D. Immunoprecipitates obtained with anti-FLAG antibody were immunoblotted and probed with anti-eIF5A antibody (BD). WCE equivalent to 5% of the input was immunoblotted as a further control. Reciprocally, the interaction between endogenous eIF5A and tagged DOHH was inhibited by CPX and DEF (FIG. 2E, right). Similarly, the interaction of endogenous eIF5A with tagged DHS was inhibited by GC7 (FIG. 2E, left), but was resistant to CPX and DEF (not shown).

These results demonstrate that CPX and DEF, but not P2 or DFOX, target DOHH and inhibit its interaction with its substrate, deoxyhypusyl-eIF5A. Despite divergent chemical structures, CPX and DEF both act as potent inhibitors of eIF5A maturation in cells and in vitro. DEF is in clinical use as an orally active medicinal chelator for treatment of transfusion-related iron overload, and CPX is employed as a topical antifungal. After oral medication, the concentration of DEF in serum can reach and exceed 250 μM. The topical preparations of CPX, which contain up to 57.5 mM of the agent, achieve levels in excess of 30 μM in skin. These results were obtained at 250 μM DEF and 30 μM CPX, concentrations well within the range of the compounds' clinically relevant levels. At these concentrations, CPX and DEF can reduce bioavailable intracellular iron levels as determined with an iron-sensitive reporter system. Agent P2, a bidentate chelation homolog of CPX lacking its hydrophobic cyclohexyl group, displayed little or no activity in cell-based assays. Thus, the inhibitory action of CPX and DEF on eIF5A is not merely a consequence of their ability to coordinate and deplete bioavailable iron by bidentate chelation.

Figure 2:
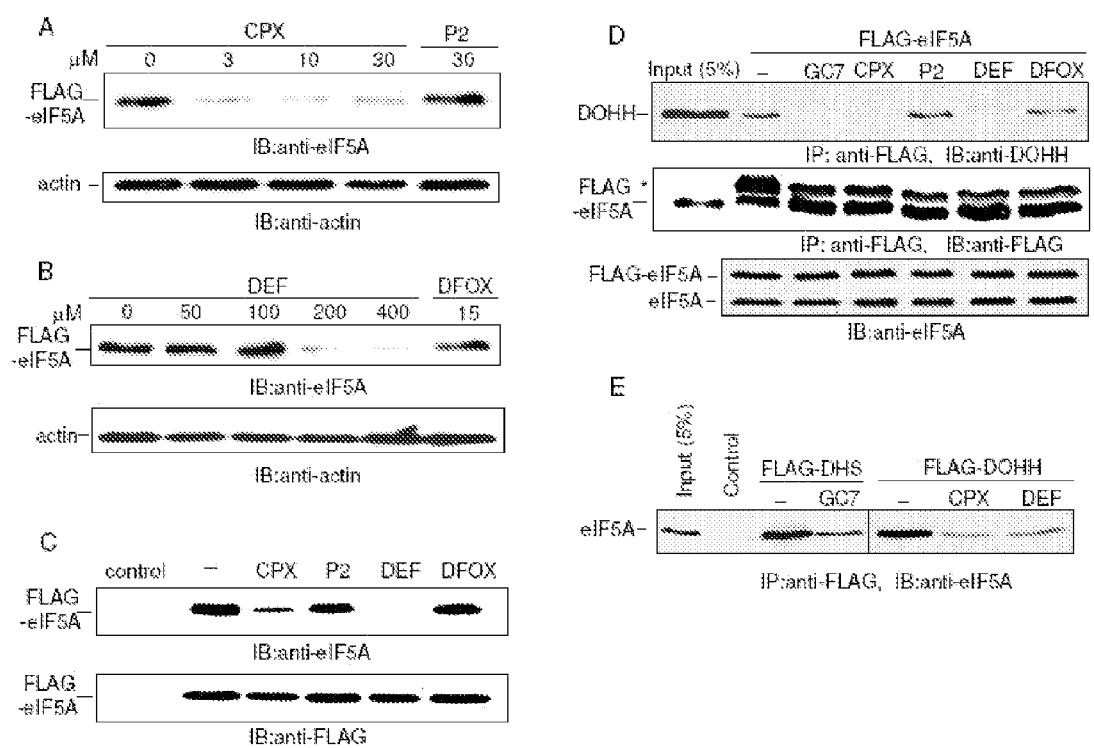
FIG. 2 illustrates the effects of ciclopirox and deferiprone on eIF5A and DOHH.
Figure 3:
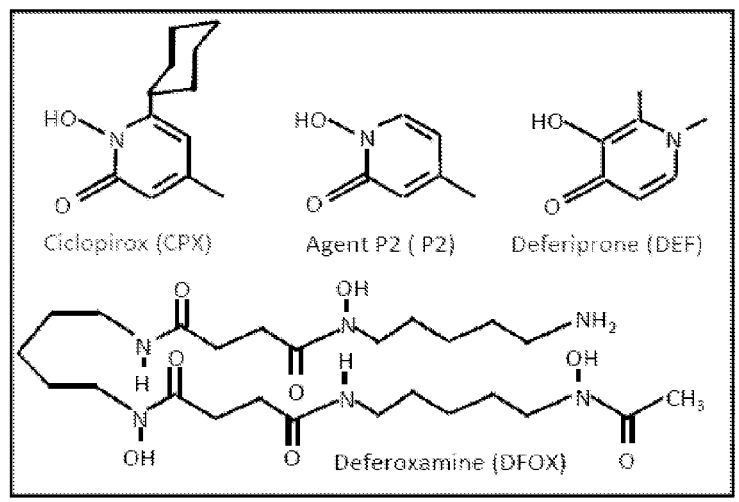
FIG. 3 illustrates various compounds and control compounds that can be used to demonstrate inhibition of eIF5A.

CPX and DEF destabilized the interaction between DOHH and deoxyhypusyl-eIF5A, resulting in a marked decrease in the appearance of newly synthesized mature eIF5A (FIG. 2). The drugs did not prevent eIF5A from forming a complex with DHS, which is consistent with the accumulation of deoxyhypusyl-eIF5A in the presence of either drug at concentrations that completely blocked DOHH activity. Neither DFOX nor P2 had any effect on the binding of eIF5A to DOHH, in accordance with their failure to inhibit the formation of hypusinyl-eIF5A. On the other hand, the DHS inhibitor GC7 blocked formation of lysyl-eIF5A:DHS complexes, causing a marked decrease in the levels of deoxyhypusyl-eIF5A and its complexes with DOHH. These findings, supported by molecular modeling, indicate that CPX and DEF enter the deoxyhypusine-binding pocket of DOHH, become oriented towards its catalytic iron atom and chelate it. The compound-iron chelate is then released from the apoenzyme, which irreversibly collapses into a catalytically inactive molecule incapable of binding substrate. Supporting this mechanism, DEF is known to cause release of peptide-bound iron from several non-heme metalloproteins, among them mono- and diferric transferrin, cyclooxygenase, and lipoxygenase.

Figure 4:
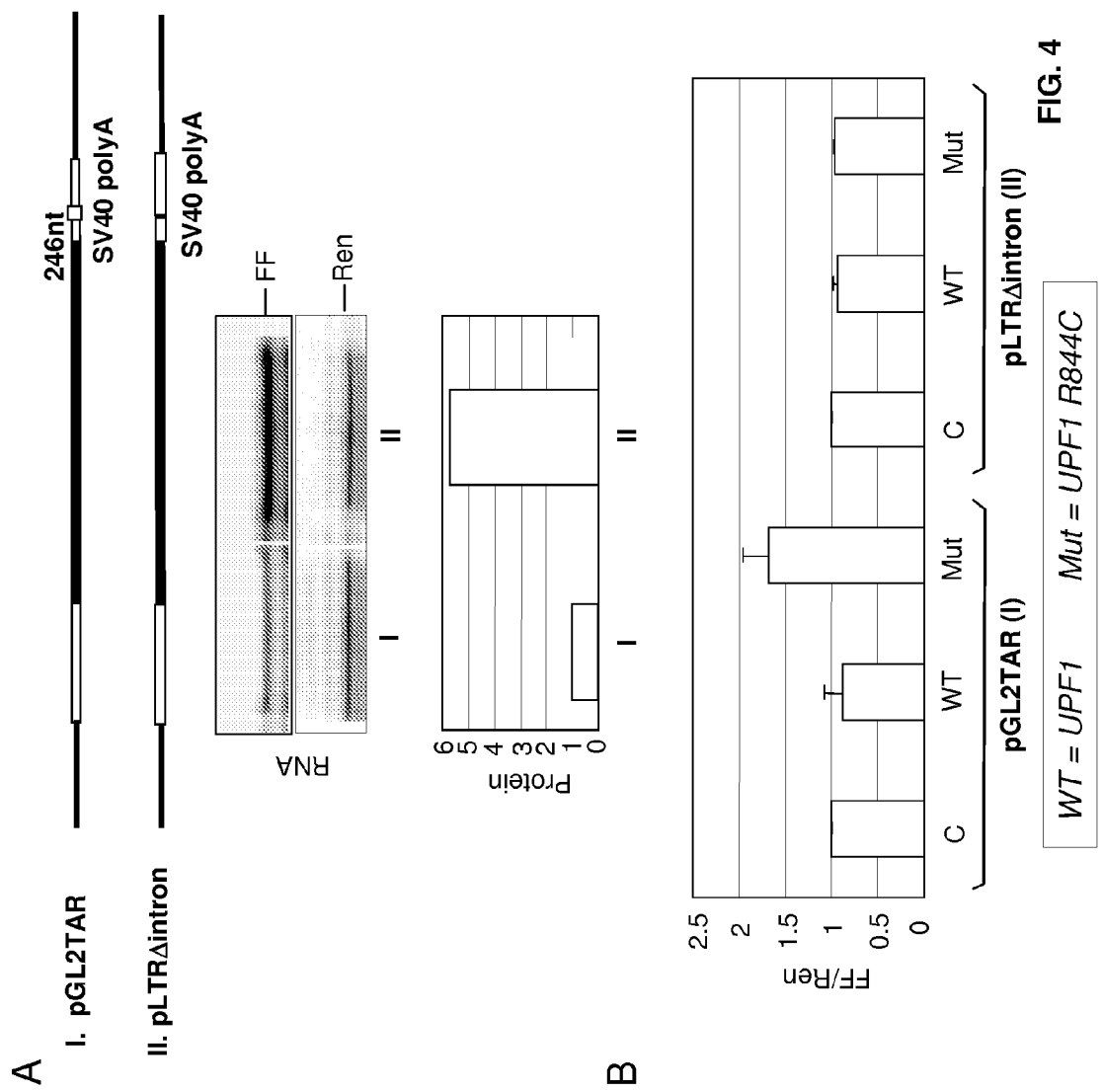
FIG. 4 demonstrates that NMD decreases gene expression at both the RNA and protein levels.

Example 2: NMD Decreases Gene Expression at Both the RNA and Protein Levels, an Effect Relieved by Inhibitors of NMD Human 293 cells were co-transfected with a test plasmid (construct I) that is sensitive to NMD and a matched control plasmid (construct II). The constructs contain firefly luciferase (FF) reporter genes and are based on studies in the HIV-1 system (Hoque M, Hanauske-Abel H M, Palumbo P, Saxena D, D'Alliessi Gandolfi D, Park M H, Pe'ery T, Mathews M B. Retrovirology. 2009 Oct. 13; 6:90). A plasmid expressing *Renilla* luciferase (Ren) directed by the CMV promoter was included as a reference and internal control. RNA was analyzed by Rnase protection assay and an autoradiograph of the results is shown. More FF RNA was generated from the NMD-insensitive construct pLTRΔintron (construct II) than from the NMD-sensitive construct pGL2TAR (construct I) (FIG. 4A). Similar observations were made at the protein level. Luciferase proteins were analyzed by dual luciferase assay kit (Promega) and the data are illustrated as the firefly: *Renilla* ratio. An inactive (dominant negative) mutant of the Upf1 protein (UPF1 R844C), whose wild-type is known to be required for NMD, inhibited NMD in this construct system (FIG. 4B). The results are shown as firefly:
*Renilla* luciferase ratio (FF/Ren). Taken together, these data verify that the assay is measuring NMD.

Figure 5:
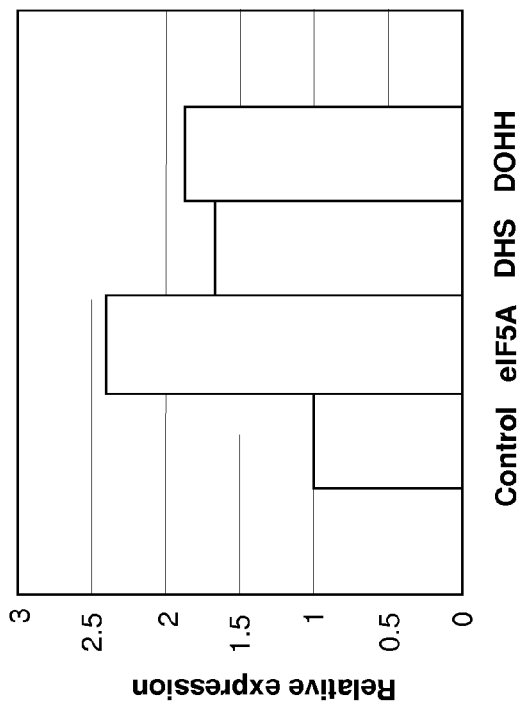
FIG. 5 demonstrates that depletion of eIF5A, DHS or DOHH inhibited NMD and therefore increased gene expression from the NMD-sensitive construct in U2OS human osteosarcoma cells.
Figure 5:
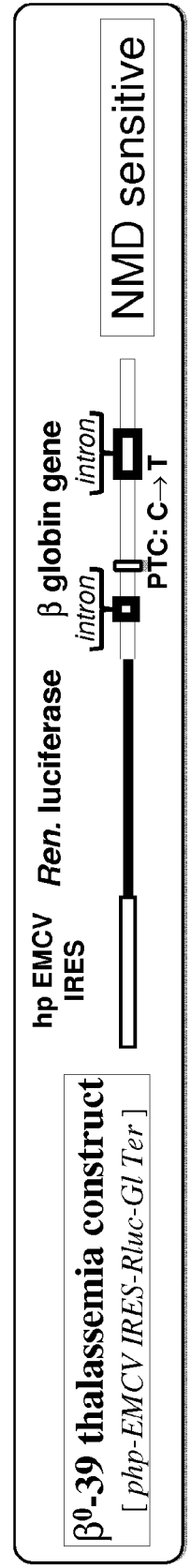

It was important to demonstrate that hypusine-modified eIF5A is involved in NMD. The experiment of FIG. 5 used RNA silencing with small interfering RNAs (siRNAs) to deplete eIF5A itself, or either of the modifying enzymes required for hypusine formation. Depletion of U2OS human osteosarcoma cells for eIF5A, DHS or DOHH inhibited NMD and therefore increased gene expression from the NMD-sensitive construct. Data are shown as ratio of luciferase activities. Similar results were obtained with a plasmid (Woeller C F, Gaspari M, Isken O, Maquat L.: EMBO Rep. 2008 May; 9(5):446-51) containing a naturally-occurring mutation highly relevant for inherited human diseases, β⁰-39 thalassemia in which the β-globin gene displays a premature termination codon (PTC) due to a C-to-T transition (FIG. 6), the most frequent mutation in the Mediterranean and South American littoral of thalassemia. On a global scale, thalassemia is one of the most common single-gene inherited conditions and was ranked by the World Health Organization as a major health problem (Weatherall, D. J. et al. 2001. Inherited haemoglobin disorders: an increasing global health problem. Bull World Health Organ 79:704-712.) These results show that hypusine-containing eIF5A is involved in the NMD process underlying β⁰-39 thalassemia.

Figure 6:
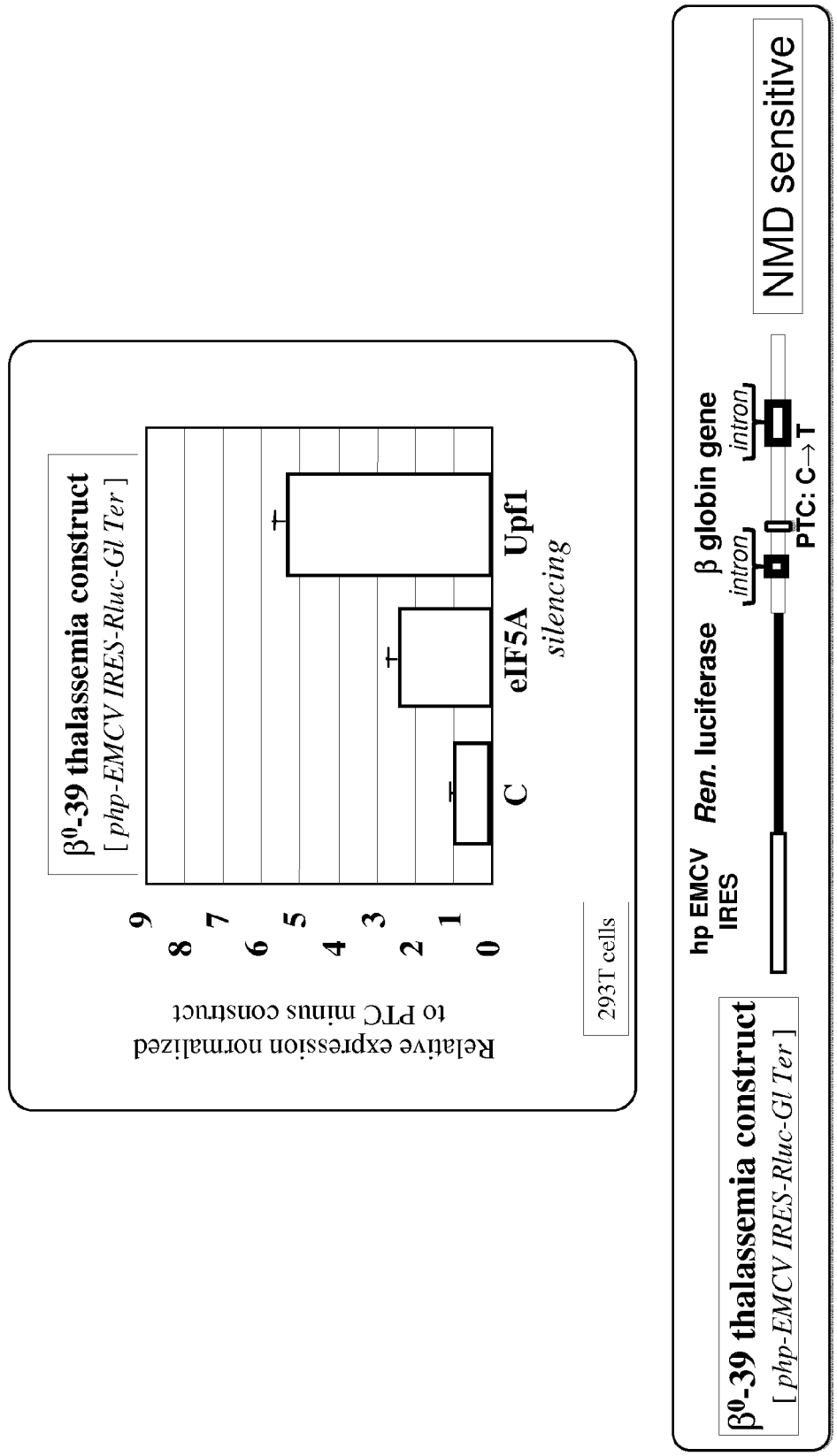
FIG. 6 demonstrates that NMD is inhibited by the drugs CPX and DEF, which prevent eIF5A modification.
Figure 7:
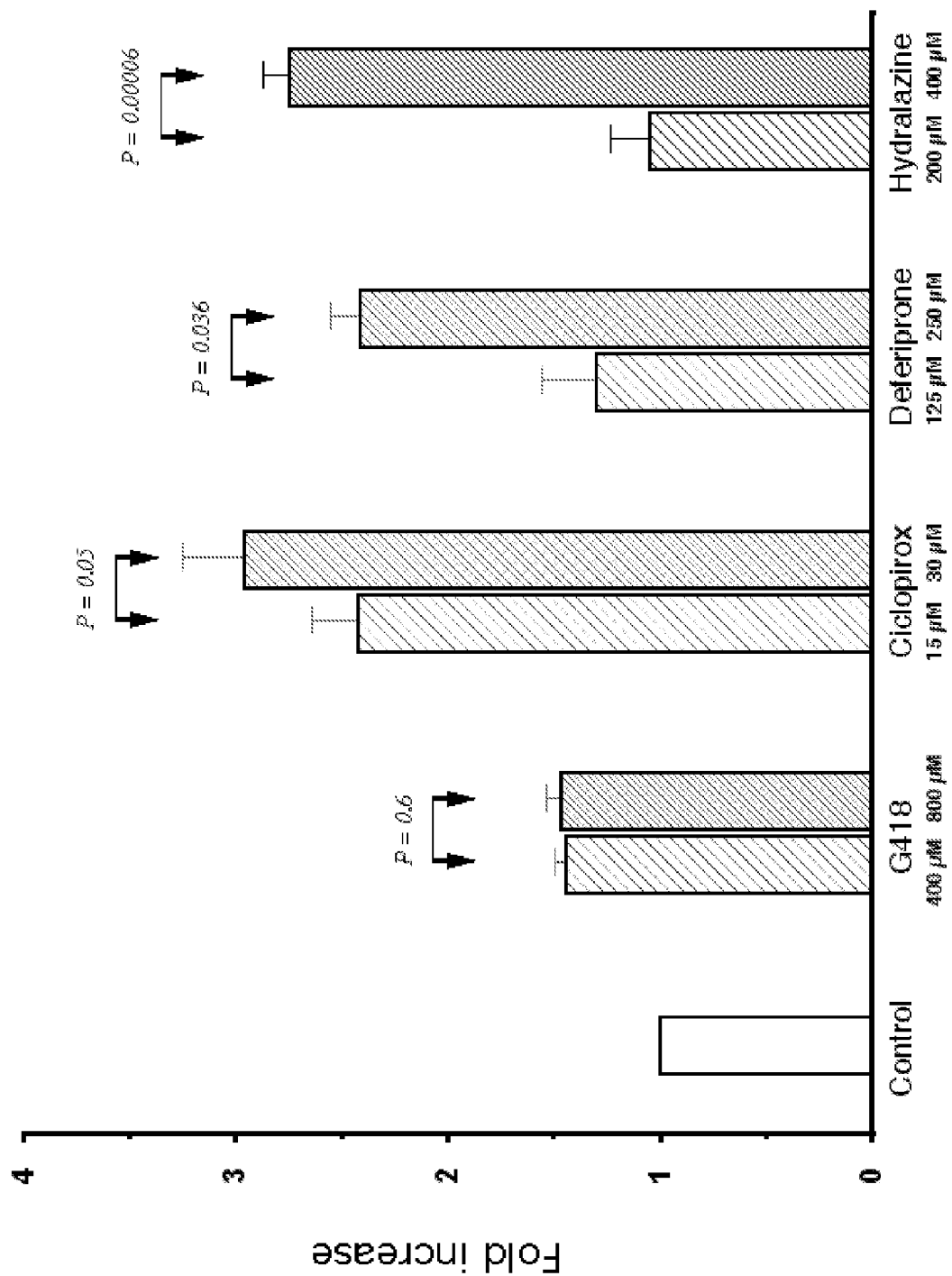
FIG. 7 shows that NMD in the thalassemia model system of FIG. 6 is inhibited by the drugs ciclopirox (CPX), deferiprone (DEF), and hydralazine (HYD) which all prevent eIF5A modification, resulting in increased gene expression.

FIG. 7 shows that NMD in the thalassemia model system of FIG. 6 is inhibited by the drugs ciclopirox (CPX), deferiprone (DEF), and hydralazine (HYD) which all prevent eIF5A modification, resulting in increased gene expression. This inhibition of NMD is seen at drug concentrations that in a dose-dependent manner interfere with DOHH function, namely 15/30 µM CPX, 125/250 µM DEF, and 200/400 µM HYD. These experiments were carried out in the well-authenticated assay system using vectors containing NMD signals associated with β⁰39-thalassemia (Woeller C F, Gaspari M, Isken O, Maquat L.: EMBO Rep. 2008 May; 9(5):446-51). For comparison, the expression-enhancing effect of the nonsense suppressor G418, an aminoglycoside, is shown (Salvatori F et al.: Am. J. Hematol. 2009, 84:720-728). Results are presented as a ratio of Renilla luciferase from the NMD-sensitive reporter to a matched NMD-insensitive control.

Figure 8:
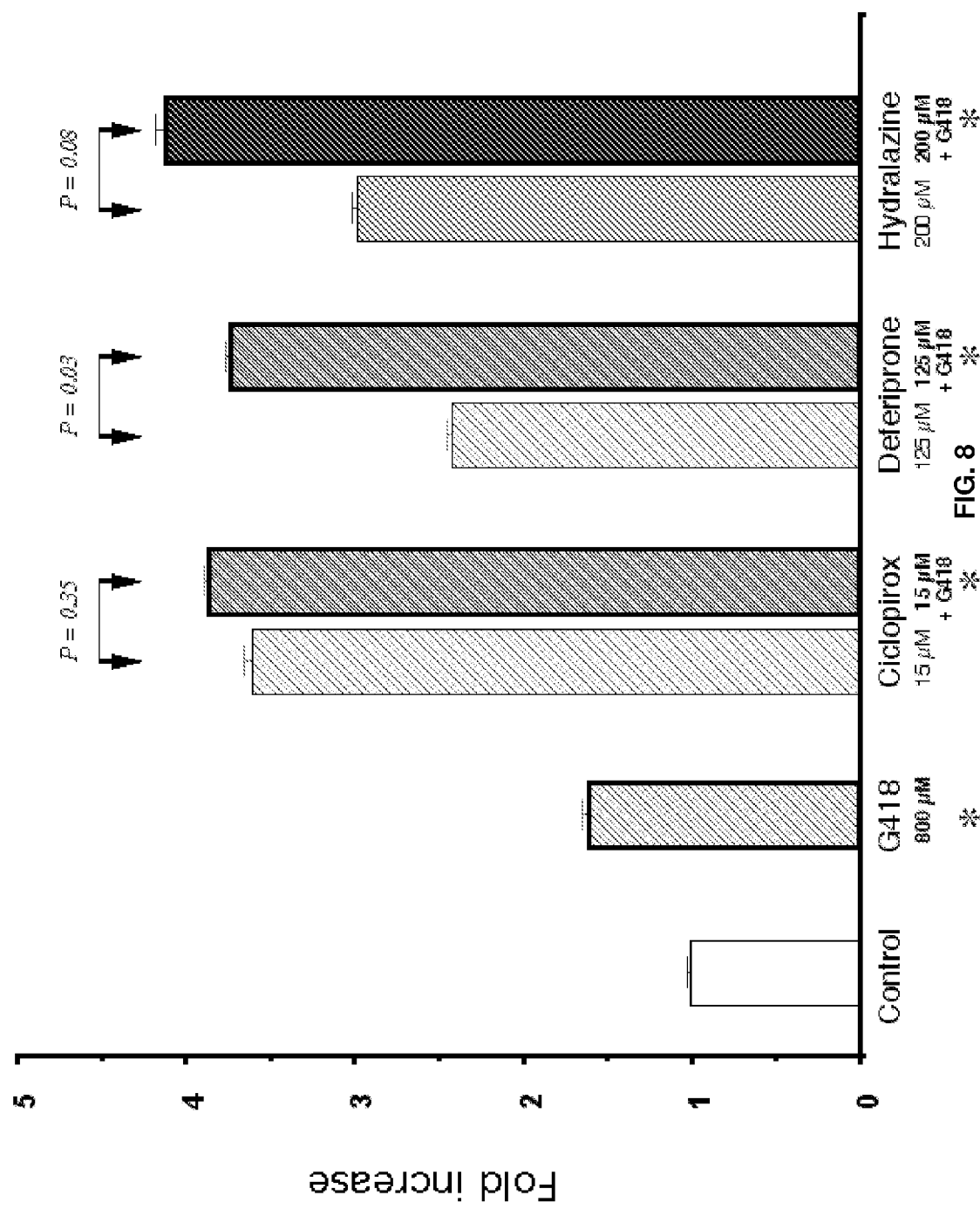
FIG. 8 shows the effect of combining an NMD inhibitor at submaximally effective concentrations (15 μM CPX; 125 μM DEF; 200 μM HYD [comp.

FIG. 8 shows the effect of combining an NMD inhibitor at submaximally effective concentrations (15 µM CPX; 125 µM DEF; 200 µM HYD [comp. FIG. 7]) with a nonsense suppressor, exemplified by G418, in this example used at 800 µM. In each case, the submaximal effect of the NMD inhibitor is distinctly enhanced, and the combination uniformly exceeds the effect of monotherapy with a nonsense suppressor by at least a factor of 2.

Figure 9:
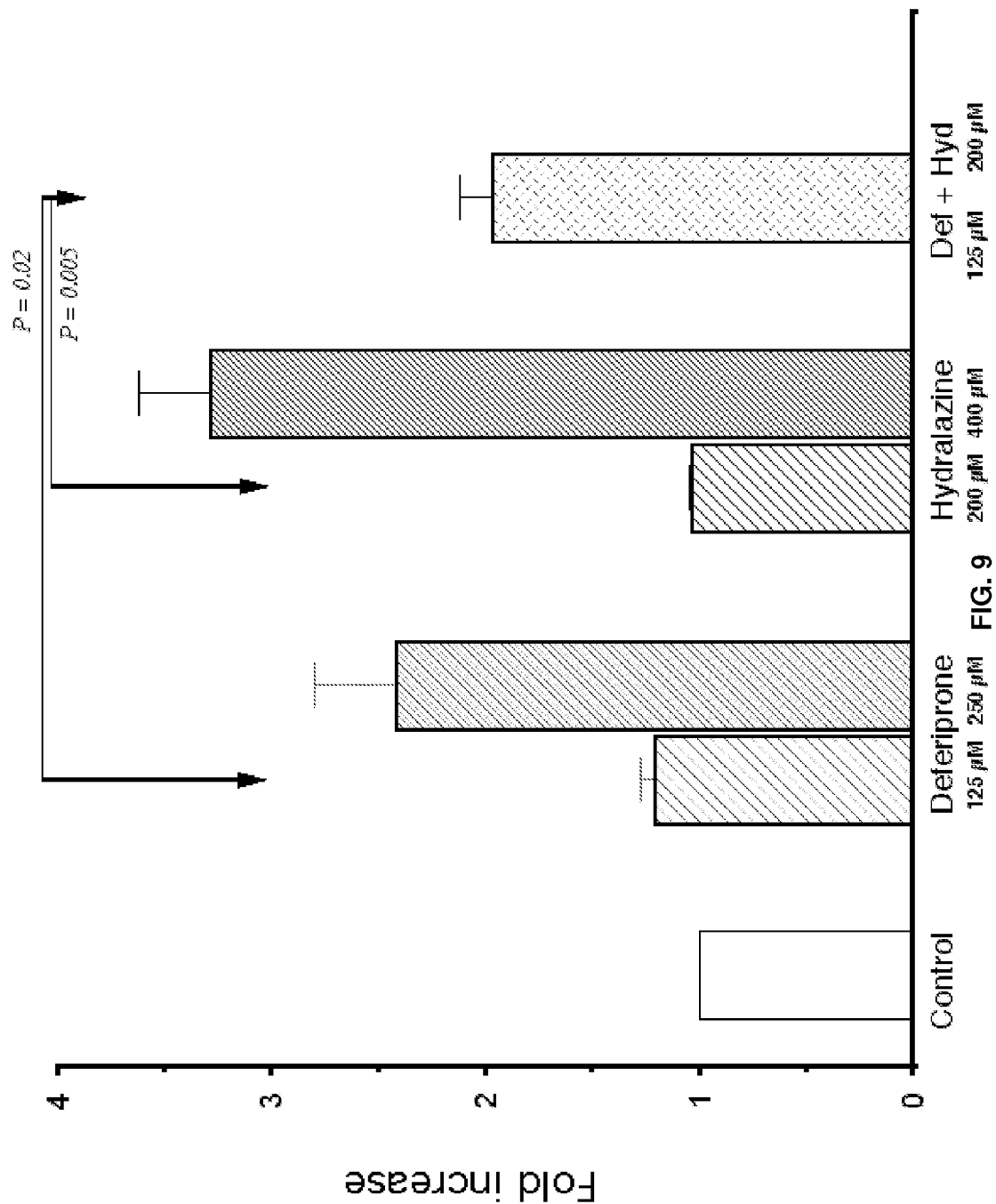
FIG. 9 exemplifies the effect of combining several NMD inhibitors, each at a concentration ineffective for NMD inhibition, in order to achieve a degree of NMD inhibition that achieves statistical significance. In the example shown, DEF at 125 μM and HYD at 200 μM, each compound ineffective, reach effectiveness when combined.

FIG. 9 exemplifies the effect of combining several NMD inhibitors, each at a concentration ineffective for NMD inhibition, in order to achieve a degree of NMD inhibition that reaches statistical significance. In the example shown, DEF at 125 µM and HYD at 200 µM, each compound ineffective individually, reach effectiveness when combined.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

What is claimed is:

1. A method for inhibiting nonsense-mediated messenger RNA (mRNA) decay (NMD) in a mammalian subject having a Nonsense-Associated Disease (NAD) comprising:
   1) identifying the mammalian subject as having a Nonsense-Associated Disease (NAD), the Nonsense-Associated Disease comprising a genetic disorder wherein a gene in the mammalian subject has a premature stop codon which results in a loss of protein function and a reduction in mRNA levels;
   2) administering to the mammalian subject having the Nonsense-Associated Disease (NAD) an effective amount of composition comprising an iron chelator which inhibits the activity of deoxyhypusine hydroxylase (DOHH), said iron chelator comprising a compound selected from the group consisting of formula (I), (III), and (IV)

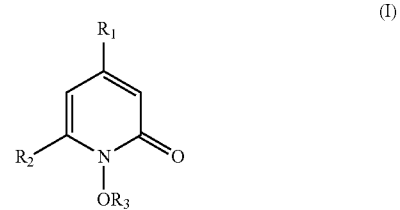

wherein
R1 is (C1-C6) alkyl;
R2 is (C1-C10) straight or branched alkyl, (C3-C6)cycloalkyl or phenoxy(C1-C3)alkyl,
where the phenoxy group is substituted by a substituted or unsubstituted phenoxy; and
R3 is hydrogen or a cation moiety to form a pharmacologically acceptable salt;

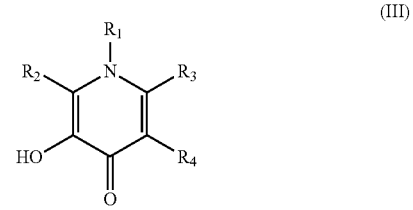

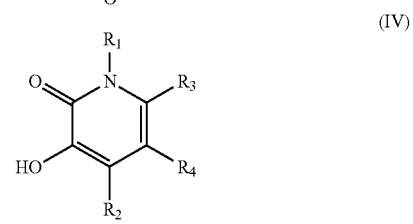

wherein R1, R2, R3, and R4 each individually represent a hydrogen, an alkyl, alkenyl, or alkoxy group containing 1 to about 8 carbon atoms, an aryl, arylaklyl, or cycloalkyl group containing about 5 to 12 carbon atoms, or a peptide or peptidomimetic moiety containing 10 to about 30 carbon atoms, wherein inhibiting the activity of deoxyhypusine hydroxylase (DOHH) results in suppressing hypusination of eIF5A protein, and suppressing hypusination of eIF5A protein results in inhibiting nonsense-mediated messenger RNA (mRNA) decay (NMD), and 3) administering to the mammalian subject a composition comprising a nonsense suppressor, whereby degradation of NMD-susceptible mRNA is decreased and translation termination at a misplaced nonsense codon is reduced.

2. The method of claim 1, wherein the iron chelator is administered with at least one additional structurally distinct iron chelator of formula (I), (III), or (IV), each administered at a low end NMD-non-inhibitory concentration, which combined inhibits NMD.

3. The method of claim 1, wherein said compound of formula (III) or (IV) is selected from the group consisting of deferiprone and its analogues.

4. The method of claim 1, wherein said nonsense suppressor is a compound of formula (VI):

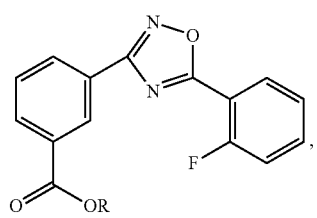 (VI)
wherein R is hydrogen, alkyl, aryl, or arylalkyl.
5. The method of claim 4 wherein said compound of formula (VI) is selected from the group consisting of Ataluren and its analogs.
* * * * *